(12) United States Patent
McDonald et al.

(10) Patent No.: US 7,150,747 B1
(45) Date of Patent: Dec. 19, 2006

(54) ELECTROSURGICAL CUTTER

(75) Inventors: Christopher McDonald, Somerville, MA (US); Michael A. Brodsky, Hillsboro, NH (US); Karen Drucker, Danville, NH (US); Albert R. Lopes, Jr., Derry, NH (US); Douglas D. Sjostrom, Tewksbury, MA (US)

(73) Assignee: Smith & Nephew, Inc., Andover, MA (US)

( * ) Notice: Subject to any disclaimer, the term of this patent is extended or adjusted under 35 U.S.C. 154(b) by 250 days.

(21) Appl. No.: 10/348,343

(22) Filed: Jan. 22, 2003

(51) Int. Cl.
*A61B 18/18* (2006.01)

(52) U.S. Cl. .......................... 606/45; 606/49; 606/180

(58) Field of Classification Search ................. 606/41, 606/45–52, 170, 180, 181; 604/21, 22, 35
See application file for complete search history.

(56) References Cited

U.S. PATENT DOCUMENTS

| | | |
|---|---|---|
| 1,952,617 A | 3/1934 | Wappler |
| 2,004,559 A | 6/1935 | Wappler et al. |
| 2,090,923 A | 8/1937 | Wappler |
| 3,178,728 A | 4/1965 | Christensen |
| 3,579,643 A | 5/1971 | Morgan |
| 3,776,230 A | 12/1973 | Neefe |
| 3,815,604 A | 6/1974 | O'Malley et al. |
| 3,856,015 A | 12/1974 | Iglesias |
| 3,867,728 A | 2/1975 | Substad et al. |
| 3,879,767 A | 4/1975 | Substad |
| 3,886,600 A | 6/1975 | Kahn et al. |
| 3,938,198 A | 2/1976 | Kahn et al. |
| 3,945,375 A | 3/1976 | Banko |
| 3,987,499 A | 10/1976 | Scharbach et al. |
| 3,992,725 A | 11/1976 | Homsy |
| 4,043,342 A | 8/1977 | Morrison, Jr. |
| 4,074,718 A | 2/1978 | Morrison, Jr. |
| 4,085,466 A | 4/1978 | Goodfellow et al. |
| 4,129,470 A | 12/1978 | Homsy |
| 4,134,406 A | 1/1979 | Iglesias |
| 4,203,444 A | 5/1980 | Bonnell et al. |
| 4,224,696 A | 9/1980 | Murray et al. |
| 4,224,697 A | 9/1980 | Murray et al. |
| 4,326,529 A | 4/1982 | Doss et al. |
| 4,344,193 A | 8/1982 | Kenny |

(Continued)

FOREIGN PATENT DOCUMENTS

DE    3511107 A1    10/1986

(Continued)

OTHER PUBLICATIONS

Attachment I: Competitive Literature on Generators with Bipolar Capabilities, IME Co., Ltd., pp. 60-86.

(Continued)

*Primary Examiner*—Michael Peffley
(74) *Attorney, Agent, or Firm*—Fish & Richardson P.C.

(57) ABSTRACT

One surgical device includes a first member and a second member defining a lumen for receiving the first member. The first member is configured to be movable relative to the second member to cut tissue. An electrical connector is physically and electrically coupled to the second member, to electrically couple the second member to a source of electricity. A tension device holds a distal region of the first member in electrical contact with a distal region of the second member. The first member includes a blade used both to cut tissue mechanically, and to coagulate cut tissue. The blade is electrically conductive and serves as an active electrode in a bipolar arrangement with a return electrode. Electrical energy is transferred to the blade through a point contact at a distal tip of the first and second members.

47 Claims, 13 Drawing Sheets

U.S. PATENT DOCUMENTS

| | | | |
|---|---|---|---|
| 4,362,160 A | 12/1982 | Hiltebrandt | |
| 4,375,220 A | 3/1983 | Matvias | |
| 4,381,007 A | 4/1983 | Doss | |
| 4,397,314 A | 8/1983 | Vaguine | |
| 4,476,862 A | 10/1984 | Pao | |
| 4,483,338 A | 11/1984 | Bloom et al. | |
| 4,517,965 A | 5/1985 | Ellison | |
| 4,517,975 A | 5/1985 | Garito et al. | |
| 4,522,206 A | 6/1985 | Whipple et al. | |
| 4,532,924 A | 8/1985 | Auth et al. | |
| 4,590,934 A | 5/1986 | Malis et al. | |
| 4,593,691 A | 6/1986 | Lindstrom et al. | |
| 4,597,379 A | 7/1986 | Kihn et al. | |
| 4,601,705 A | 7/1986 | McCoy | |
| 4,651,734 A | 3/1987 | Doss et al. | |
| 4,662,371 A | 5/1987 | Whipple et al. | |
| 4,705,038 A | 11/1987 | Sjostrom et al. | |
| 4,747,821 A | 5/1988 | Kensey et al. | |
| 4,811,733 A | 3/1989 | Borsanyi et al. | |
| 4,815,462 A * | 3/1989 | Clark | 606/170 |
| 4,819,633 A * | 4/1989 | Bauer et al. | 606/52 |
| 4,834,729 A | 5/1989 | Sjostrom | |
| 4,838,859 A | 6/1989 | Strassmann | |
| 4,846,175 A | 7/1989 | Frimberger | |
| 4,873,976 A | 10/1989 | Schreiber | |
| 4,894,063 A | 1/1990 | Nashef | |
| 4,895,148 A | 1/1990 | Bays et al. | |
| 4,907,585 A | 3/1990 | Schachar | |
| 4,907,589 A | 3/1990 | Cosman | |
| 4,924,865 A | 5/1990 | Bays et al. | |
| 4,944,727 A | 7/1990 | McCoy | |
| 4,950,234 A | 8/1990 | Fujioka et al. | |
| 4,955,882 A | 9/1990 | Hakky | |
| 4,966,597 A | 10/1990 | Cosman | |
| 4,976,709 A | 12/1990 | Sand | |
| 4,976,715 A | 12/1990 | Bays et al. | |
| 4,983,179 A | 1/1991 | Sjostrom | |
| 4,998,527 A | 3/1991 | Meyer | |
| 4,998,933 A | 3/1991 | Eggers et al. | |
| 5,007,908 A | 4/1991 | Rydell | |
| 5,009,656 A | 4/1991 | Reimels | |
| 5,024,659 A | 6/1991 | Sjostrom | |
| 5,085,657 A | 2/1992 | Ben-Simhon | |
| 5,085,659 A | 2/1992 | Rydell | |
| 5,098,430 A | 3/1992 | Fleenor | |
| 5,098,431 A | 3/1992 | Rydell | |
| 5,100,402 A | 3/1992 | Fan | |
| 5,103,804 A | 4/1992 | Abele et al. | |
| 5,112,330 A | 5/1992 | Nishigaki et al. | |
| 5,114,402 A | 5/1992 | McCoy | |
| 5,133,729 A | 7/1992 | Sjostrom | |
| 5,147,357 A * | 9/1992 | Rose et al. | 606/49 |
| 5,152,748 A | 10/1992 | Chastagner | |
| 5,171,311 A | 12/1992 | Rydell et al. | |
| 5,178,620 A | 1/1993 | Eggers et al. | |
| 5,186,181 A | 2/1993 | Franconi et al. | |
| 5,191,883 A | 3/1993 | Lennox et al. | |
| 5,192,267 A | 3/1993 | Shapira et al. | |
| 5,201,729 A | 4/1993 | Hertzmann et al. | |
| 5,201,730 A | 4/1993 | Easley et al. | |
| 5,201,731 A | 4/1993 | Hakky | |
| 5,213,097 A | 5/1993 | Zeindler | |
| 5,230,334 A | 7/1993 | Klopotek | |
| 5,242,439 A | 9/1993 | Larsen et al. | |
| 5,242,441 A | 9/1993 | Avitall | |
| 5,250,047 A | 10/1993 | Rydell | |
| 5,257,990 A | 11/1993 | Nash | |
| 5,261,906 A | 11/1993 | Pennino et al. | |
| 5,267,994 A | 12/1993 | Gentelia et al. | |
| 5,275,151 A | 1/1994 | Shockey et al. | |
| 5,279,559 A | 1/1994 | Barr | |
| 5,281,220 A * | 1/1994 | Blake, III | 606/46 |
| 5,284,479 A | 2/1994 | de Jong | |
| RE34,556 E | 3/1994 | Sjostrom et al. | |
| 5,290,282 A | 3/1994 | Casscells | |
| 5,304,169 A | 4/1994 | Sand | |
| 5,306,238 A | 4/1994 | Fleenor | |
| 5,308,311 A | 5/1994 | Eggers et al. | |
| 5,311,858 A | 5/1994 | Adair | |
| 5,318,564 A | 6/1994 | Eggers | |
| 5,320,115 A | 6/1994 | Kenna | |
| 5,323,778 A | 6/1994 | Kandarpa et al. | |
| 5,324,254 A | 6/1994 | Phillips | |
| 5,334,140 A | 8/1994 | Phillips | |
| 5,334,193 A | 8/1994 | Nardella | |
| 5,342,357 A | 8/1994 | Nardella | |
| 5,348,554 A | 9/1994 | Imran et al. | |
| 5,352,868 A | 10/1994 | Denen et al. | |
| 5,354,311 A | 10/1994 | Kambin et al. | |
| 5,354,331 A | 10/1994 | Schachar | |
| 5,364,395 A * | 11/1994 | West, Jr. | 606/46 |
| 5,366,443 A | 11/1994 | Eggers et al. | |
| 5,366,490 A | 11/1994 | Edwards et al. | |
| 5,380,277 A | 1/1995 | Phillips | |
| 5,382,247 A | 1/1995 | Cimino et al. | |
| 5,395,312 A | 3/1995 | Desai | |
| 5,397,304 A | 3/1995 | Truckai | |
| 5,401,272 A | 3/1995 | Perkins | |
| 5,413,575 A | 5/1995 | Haenggi | |
| 5,415,633 A | 5/1995 | Lazarus et al. | |
| 5,423,806 A | 6/1995 | Dale et al. | |
| 5,433,739 A | 7/1995 | Sluijter et al. | |
| 5,437,661 A | 8/1995 | Rieser | |
| 5,437,662 A | 8/1995 | Nardella | |
| 5,451,223 A | 9/1995 | Ben-Simhon | |
| 5,456,689 A | 10/1995 | Kresch et al. | |
| 5,458,596 A | 10/1995 | Lax et al. | |
| 5,464,023 A | 11/1995 | Viera | |
| 5,465,737 A | 11/1995 | Schachar | |
| 5,484,403 A | 1/1996 | Yoakum et al. | |
| 5,484,432 A | 1/1996 | Sand | |
| 5,484,435 A | 1/1996 | Fleenor et al. | |
| 5,487,757 A | 1/1996 | Truckai et al. | |
| 5,498,258 A | 3/1996 | Hakky et al. | |
| 5,500,012 A | 3/1996 | Brucker et al. | |
| 5,507,812 A | 4/1996 | Moore | |
| 5,514,130 A | 5/1996 | Baker | |
| 5,524,338 A | 6/1996 | Martyniuk et al. | |
| 5,527,331 A | 6/1996 | Kresch et al. | |
| 5,542,920 A | 8/1996 | Cherif Cheikh | |
| 5,569,164 A | 10/1996 | Lurz | |
| 5,569,242 A | 10/1996 | Lax et al. | |
| 5,569,244 A | 10/1996 | Hahnen | |
| 5,582,810 A | 12/1996 | Tretjak | |
| 5,599,345 A | 2/1997 | Edwards et al. | |
| 5,599,346 A | 2/1997 | Edwards et al. | |
| 5,599,349 A | 2/1997 | D'Amelio | |
| 5,602,449 A | 2/1997 | Krause et al. | |
| 5,630,839 A | 5/1997 | Corbett, III et al. | |
| 5,634,924 A | 6/1997 | Turkel et al. | |
| D381,425 S | 7/1997 | Cesarini et al. | |
| 5,665,062 A | 9/1997 | Houser | |
| 5,681,282 A | 10/1997 | Eggers et al. | |
| 5,683,366 A | 11/1997 | Eggers et al. | |
| 5,688,270 A | 11/1997 | Yates et al. | |
| D388,170 S | 12/1997 | Sjostrom | |
| 5,697,909 A | 12/1997 | Eggers et al. | |
| 5,712,543 A | 1/1998 | Sjostrom | |
| D390,955 S | 2/1998 | Sjostrom et al. | |
| D390,956 S | 2/1998 | Sjostrom et al. | |
| 5,718,702 A | 2/1998 | Edwards | |
| 5,730,752 A | 3/1998 | Alden et al. | |
| 5,749,885 A | 5/1998 | Sjostrom et al. | |
| 5,782,795 A | 7/1998 | Bays | |

| | | | |
|---|---|---|---|
| 5,810,809 A * | 9/1998 | Rydell | 606/49 |
| 5,814,044 A | 9/1998 | Hooven | |
| 5,871,493 A | 2/1999 | Sjostrom et al. | |
| 5,876,369 A | 3/1999 | Houser | |
| 5,904,681 A | 5/1999 | West, Jr. | |
| 5,941,876 A | 8/1999 | Nardella et al. | |
| 6,004,320 A | 12/1999 | Casscells et al. | |
| 6,007,533 A | 12/1999 | Casscells et al. | |
| 6,090,122 A | 7/2000 | Sjostrom et al. | |
| 6,159,209 A | 12/2000 | Hakky | |
| 6,193,715 B1 * | 2/2001 | Wrublewski et al. | 606/45 |
| 6,197,025 B1 | 3/2001 | Grossi et al. | |
| 6,214,001 B1 * | 4/2001 | Casscells et al. | 606/41 |
| 6,214,024 B1 | 4/2001 | Houser | |
| 6,328,752 B1 | 12/2001 | Sjostrom et al. | |
| 6,436,116 B1 | 8/2002 | Spitz et al. | |
| 6,652,522 B1 * | 11/2003 | Cucin | 606/49 |
| 2002/0082632 A1 | 6/2002 | Spitz et al. | |
| 2003/0114875 A1 | 6/2003 | Sjostrom | |

FOREIGN PATENT DOCUMENTS

| | | |
|---|---|---|
| DE | 3632197 A1 | 3/1988 |
| DE | 3918316 | 3/1990 |
| DE | 19650797 | 6/1997 |
| DE | 19641564 C1 | 5/1998 |
| EP | 0257116 A1 | 3/1988 |
| EP | 0274705 A1 | 7/1988 |
| EP | 0479482 A1 | 4/1992 |
| EP | 0521595 A2 | 1/1993 |
| EP | 0542412 A1 | 5/1993 |
| EP | 0558297 A2 | 9/1993 |
| EP | 0566450 A1 | 10/1993 |
| EP | 0572131 A1 | 12/1993 |
| EP | 0682910 A1 | 11/1995 |
| EP | 0692224 A1 | 1/1996 |
| EP | 0729730 A1 | 9/1996 |
| EP | 0733345 A1 | 9/1996 |
| EP | 0737487 A2 | 10/1996 |
| EP | 0783903 A1 | 7/1997 |
| FR | 1 122 634 | 9/1956 |
| FR | 2 645 008 | 3/1989 |
| GB | 1 340 451 | 12/1973 |
| GB | 2 164 473 | 3/1986 |
| GB | 2 179 861 | 7/1986 |
| JP | 5-42166 | 2/1993 |
| RU | 637118 | 12/1978 |
| WO | 82/02488 | 8/1982 |
| WO | 85/02762 | 7/1985 |
| WO | 90/03152 | 4/1990 |
| WO | 92/05828 | 4/1992 |
| WO | 92/10142 | 6/1992 |
| WO | 93/01774 | 2/1993 |
| WO | 93/16648 | 9/1993 |
| WO | 93/20984 | 10/1993 |
| WO | 95/01814 | 1/1995 |
| WO | 95/10981 | 4/1995 |
| WO | 95/13113 | 5/1995 |
| WO | 95/18575 | 7/1995 |
| WO | 95/20360 | 8/1995 |
| WO | 95/25471 | 9/1995 |
| WO | 95/30373 | 11/1995 |
| WO | 95/30377 | 11/1995 |
| WO | 95/34259 | 12/1995 |
| WO | 96/11638 | 4/1996 |
| WO | 96/14020 | 5/1996 |
| WO | 96/23449 | 8/1996 |
| WO | 96/32051 | 10/1996 |
| WO | 96/32885 | 10/1996 |
| WO | 96/34559 | 11/1996 |
| WO | 96/34568 | 11/1996 |
| WO | 96/34571 | 11/1996 |
| WO | 96/39914 | 12/1996 |
| WO | 97/06855 | 2/1997 |
| WO | 98/07468 | 2/1998 |
| WO | 98/17190 | 4/1998 |
| WO | 99/51158 | 10/1999 |

OTHER PUBLICATIONS

Attachment II: Competitive Literature on Bipolar Forceps and Footswitch Controls, IME Co., Ltd., pp. 87-104.

Auhll, Richard A., "The Use of the Resectoscope in Gynecology", Biomedical Business International, Oct. 11, 1990, pp. 91-93.

Beading, L., "Bi-Polar electrosurgical devices: Sculpting the future of arthroscopy", Orthopedics today, vol. 17, No. 1, Jan. 1997, 4 pages.

Bosacco et al., Functional Results of Percutaneous Laser Discectomy, Dec. 1996, pp. 825-828.

Bromm et al., Human Neurobiology: Nerve Fibre Discharges, Cerebral Potentials and Sensations Induced by CO2 laser Stimulation, vol. 3, (1984) pp. 33-40.

Buchelt et al., Lasers in Surgery and Medicine:Erb:YAG and Hol:YAG Laser Ablation of Meniscus and Intervertebral Discs, vol. 12, No. 4 (1992) pp. 375-381.

Choy et al., Percutaneous Laser Disc Decompression: A New Therapeutic Modality, vol. 17 No. 8 (1992) pp. 949-956.

Cosman et al., Theoretical Aspects of Radiofrequency lesions in the Dorsal Root Entry Zone, vol. 15, No. 6 (1984), pp. 945-950.

Davis, Early Experience with Laser Disc Decompression, vol. 79, No. 1 (1992), J. Florida M.A.

Ellman International Mfg., Inc., Mfg Inc., 1989, Catalog, pp. 1-15, 20.

Gehring, W.J., Exploring the Homeobox (1993) pp. 215-221.

Gerber et al., Der Orthopade: Offene Laserchirurgie am Bewegungsapparat, vol. 25 (1996), pp. 56-63.

Gottlob et al., Lasers in Surgery and Medicine: Holmium: YAG Laser Ablation of Human Intervertebral Disc: Preliminary Evaluation, vol. 12 (1999) pp. 86-91.

Houpt, J. et al., "Experimental Study of Temperature Distributions and Thermal Transport During Radiofrequency Current Therapy of the Intervertebral Disc", SPINE, vol. 21, No. 15, (1996), pp. 1808-1813.

Introduction to the LDD Disc Kit, Oct. 16, 1996.

Kelly, L.E., Purification and Properties of a 23kDa Ca2+-binding Protein (1990) 271, pp. 661-666.

Kilaghbian, V.A., Coagulating Arthroscopy Shaver: A New Device, 1996, 7 pgs.

Kolarik et al., Photonucleolysis of Intervertebral Disc and it's Herniation, vol. 51 (1990), pp. 69-71.

Leu et al., Der Orthopade: Endoskopie der Wirbelsaule: Minimal-invasive Therapie, vol. 21 (1992) pp. 267-272.

Mayer et al., Lasers in Percutaneous Disc Surgery: Beneficial Technology or Gimmick?, vol. 25, No. 251 (1993), pp. 38-44.

Mehta et al., The Treatment of Chronic Back Pain: A Preliminary Survey of the Effect of Radiofrequency Denervation of the Posterior Vertebral Joints, vol. 34 (1979), pp. 768-775.

Patil et al., Percutaneous Discectomy Using the Electomagnetic Field Focusing Probe: A Feasability Study.

Phillips et al., JMRI: MR Imaging of Ho: YAG Laser Diskectomy with Histologic Correlation, vol. 3, No. 3, May/Jun. 1993.

PRNewswire (Dec. 12, 1994), Two Physicians Perform First Outpatient Cervical Disc Procedure Using Laser Technology.

Quigley et al., Laser Discectomy: Comparison of Systems, vol. 19, No. 3 (1994), pp. 319-322.

Savitz, M.A., Same-day Microsurgical Arthroscopic lateral-approach Laser-assisted (SMALL) Fluoroscopic Discectomy, vol. 80, Jun. 1994, pp. 1039-1045.

Schatz et al., Preliminary Experiencce With Percutaneous Laser Disc Decompression in the Treatment of Sciatica, vol. 38, No. 5, Oct. 1995, pp. 432-436.

Sluijter et al., Persistant Pain, Modern Methods of Treatment: Treatment of Chronic Back and Neck Pain, vol. 3 (1981), pp. 141-179.

Sluijter, M.E., The Use of Radiofrequency lesions For Pain Relief in Failed Back Patients, vol. 10, No. 1 (1988).

Sminia et al., Effects of 434 MHz Microwave Hyperthermia Applied to the Rat in the Region of the Cervical Spinal Cord, vol. 3, No. 5 (1987), pp. 441-452.

Smith & Nephew, Endoscopy, Dyonics® EP-1 Disposable Arthroscopy Blades Leaflet, Instructions for Use, 1996.

Smith+Nephew, Endoscopy Division, 1998 Products Catalog, Shaver Systems, pp. C1-D8, 1998.

Smith+Nephew, Dyonics Power Shaver System Operations/Service Manual, 23 pages, Apr. 2001.

Troussier, B. et al., "Percutaneous Intradiscal Radio-Frequency Thermocoagulation: A Cadaveric Study", *SPINE*, vol. 20, No. 15, (Aug. 1995), pp. 1713-1718.

Wolgin et al., Excimer Ablation of Human Intervertebral Disc at 308 Nanometers, vol. 9 (1989), pp. 124-131.

Yonezawa et al., The System and Procedure of Percutaneous Intradiscal Laser Nucleotomy, vol. 15, No. 5 (1990) pp. 1175-1185.

\* cited by examiner

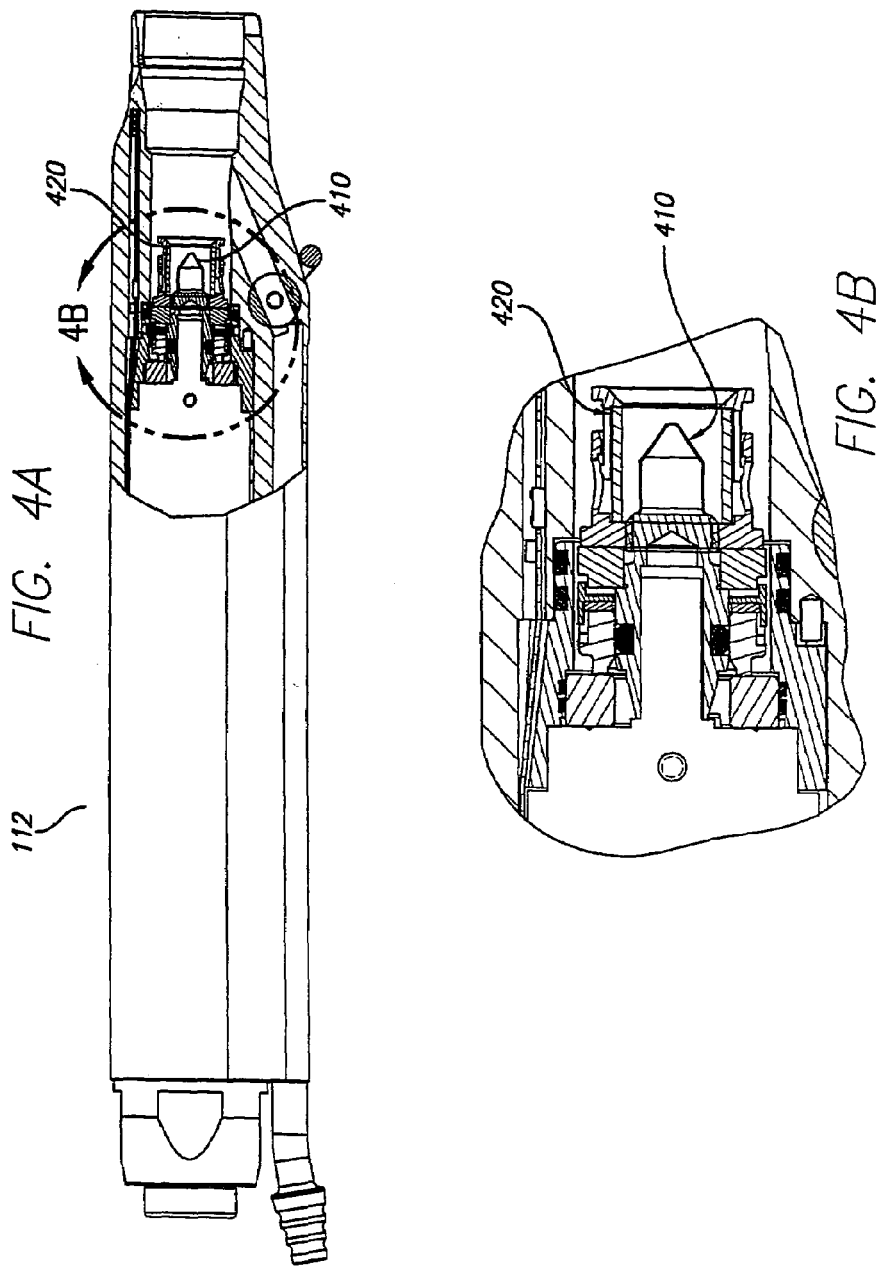

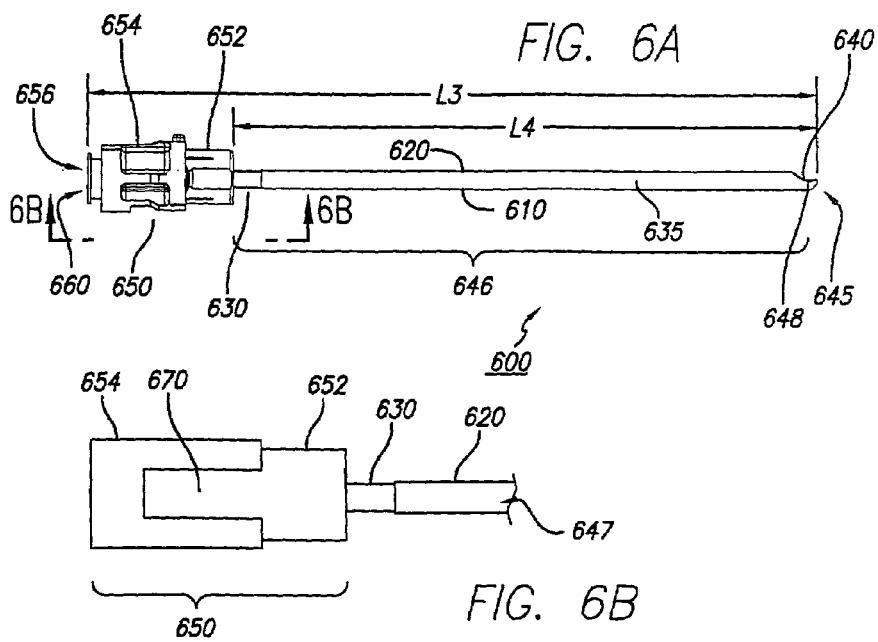
FIG. 6A
FIG. 6B
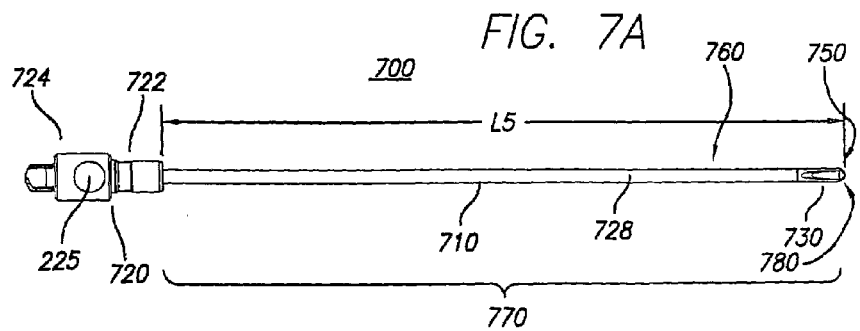
FIG. 7A
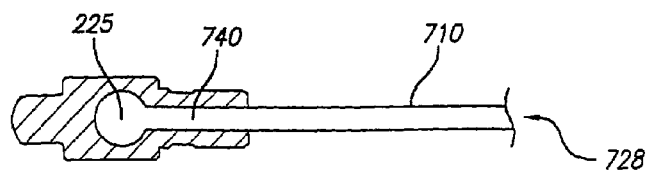
FIG. 7B

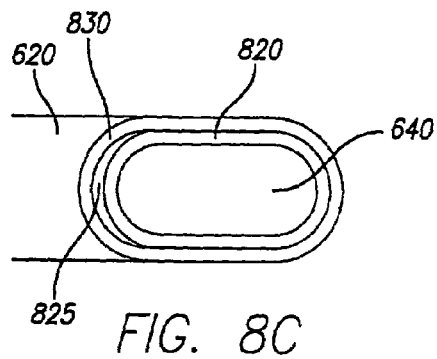
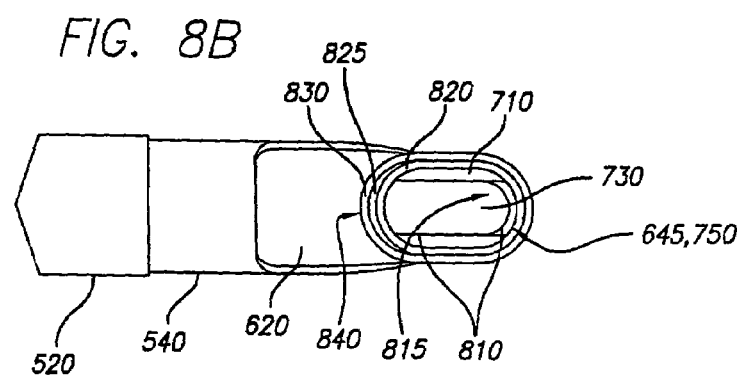
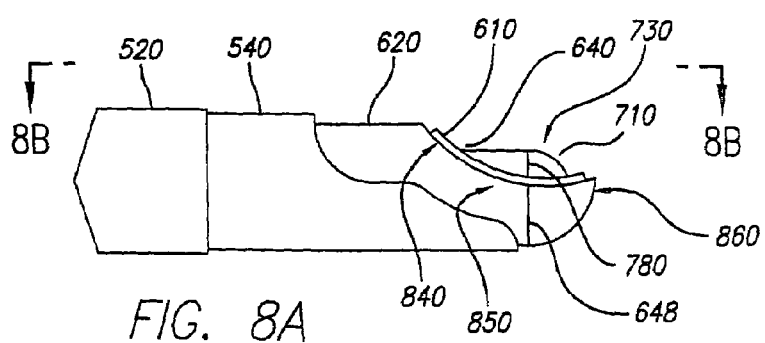

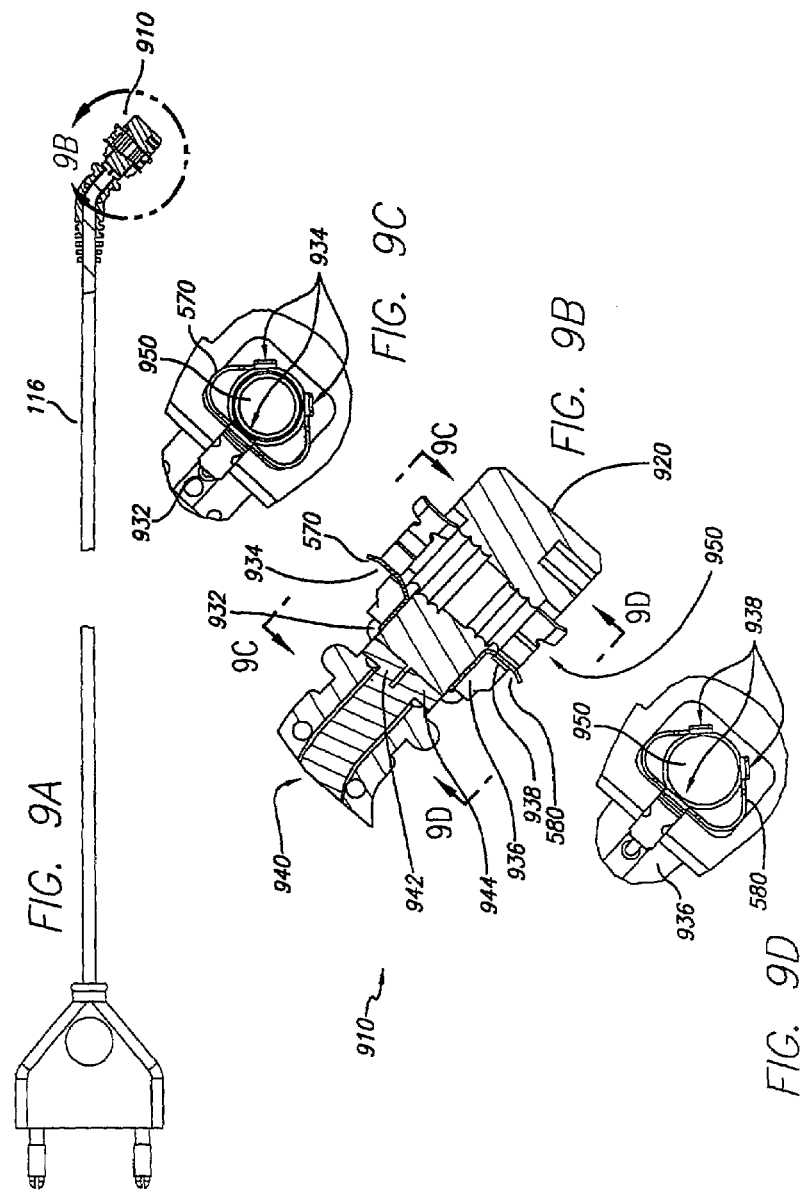

ELECTROSURGICAL CUTTER

TECHNICAL FIELD

A disclosed embodiment relates generally to arthroscopic surgery, and more particularly to a hand-held arthroscopic instrument providing an electrically conductive blade for mechanical cutting and electrosurgery.

BACKGROUND

Arthroscopic instruments can be used to cut tissue mechanically in various parts of a body, such as, for example, a knee, using a blade that is rotated, or otherwise brought into contact with the tissue to be cut. Arthroscopic instruments are also known that include a monopolar or bipolar electrode configuration for coagulating tissue using radio frequency ("RF") energy.

SUMMARY

A described embodiment provides an arthroscopic or endoscopic instrument having a blade that is used both to cut tissue mechanically and to coagulate the cut tissue. The blade is electrically conductive and serves as an active electrode in a bipolar arrangement with a return electrode located nearby on the instrument. The blade is rotated to cut the tissue mechanically, yet no brush is used to transfer electrical energy to the rotating blade. Instead, electrical energy is transferred to the blade through contact between distal tips of a non-rotating tube and a concentric rotating tube containing the blade.

According to one aspect, a surgical device includes a first member, a second member, an electrical connector, and a tension device. The second member defines a lumen for receiving the first member, the first member and second member being configured to be movable relative to each other to cut tissue. The electrical connector is physically and electrically coupled to the second member, the electrical connector being configured to electrically couple the second member to a source of electricity. The tension device is for holding a distal region of the first member in electrical contact with a distal region of the second member.

Embodiments of this aspect may include one or more of the following features.

The electrical connector is self-centering on the second member. The second member includes a tube and the electrical connector includes a three-point connector that is self-centering on the tube.

A third member is physically coupled to the second member and electrically isolated from the distal region of the first member. A first electrode is in electrical contact with the distal portion of the first member; the third member includes a second electrode; and the surgical device is operable as a bipolar electrosurgical device using the first and second electrodes. The first member includes a first tube, the second member includes a second tube that is cylindrical, and the third member includes a third tube disposed about the second tube. An exposed surface area of the second electrode is at least approximately five times larger than an exposed surface area of the first electrode.

An electrode is in electrical contact with the distal portion of the first member, and the surgical device is operable as a monopolar electrosurgical device using the electrode. The electrode is part of the first member.

The tension device holds a tip of the first member in electrical contact with a tip of the second member. The first member defines a longitudinal axis and the tension device applies tension along the longitudinal axis of the first member. The tension device includes a spring. A lock is physically coupled to the second member for coupling the second member to the tension device. A drive unit is coupled to the first member to move the first member relative to the second member, wherein the second member is fixed with respect to the drive unit.

The first member includes an electrically conductive cutting surface configured to cut tissue mechanically and to perform electrosurgery. The cutting surface includes a blade or a burr. The electrosurgery includes coagulation. The second member includes a cutting surface configured to cut tissue mechanically in cooperation with the electrically conductive cutting surface of the first member. A portion of the cutting surface of the second member is electrically conductive and is configured to perform electrosurgery along with the cutting surface of the first member. The cutting surfaces of the first member and the second member are configured to be moved past each other and to cut tissue mechanically that is disposed between the two cutting surfaces as the two cutting surfaces are moved past each other. The second member includes an electrically insulating cutting surface configured to cut tissue mechanically in cooperation with the electrically conductive cutting surface of the first member.

The first member is configured to be rotated relative to the second member to cut tissue. The first member includes a first tube, and the second member includes a second tube that is cylindrical. The first member defines an inner lumen operable as an aspiration lumen.

The first member is substantially electrically insulating, and the first member includes an electrically conductive material at the distal portion of the first member. The second member is substantially electrically insulating, and includes an electrically conductive material at the distal portion of the second member.

A drive unit is coupled to the first member to move the first member relative to the second member, and the second member is fixed with respect to the drive unit. A first electrode is in electrical contact with the distal portion of the first member, and the first electrode includes a cutting surface configured to cut tissue mechanically and to perform electrosurgery. A second electrode is physically coupled to the second member and electrically isolated from the distal region of the first member, and the distal region of the first member includes a tip of the first member and the distal region of the second member includes a tip of the second member.

According to another aspect, performing surgery includes inserting a surgical device into a body. The surgical device includes a first member and a second member, and the second member defines a lumen for receiving the first member. The first member and the second member are moved relative to each other to cut tissue. A distal region of the first member is held in electrical contact with a distal region of the second member. Electrical power is provided to the first member through the second member.

Embodiments of this aspect may include one or more of the following features.

A distal tip of the first member is maintained in electrical connection with a distal tip of the second member. Inserting the surgical device includes inserting a surgical device having an inner cutting surface on the first member and an outer cutting surface on the second member. Moving the first member and the second member relative to each other includes cutting tissue in the body using the inner cutting surface and the outer cutting surface. Providing electrical power includes performing electrosurgery on the cut tissue using the inner cutting surface.

Moving the first member and the second member relative to each other includes rotating the first member relative to the second member, such rotating causing the inner cutting surface to pass by the outer cutting surface and causing tissue disposed between the two cutting surfaces to be cut mechanically. A conductive environment is provided in the body, and inserting the surgical device into the body includes inserting the inner cutting surface into the conductive environment. Performing electrosurgery includes performing bipolar electrosurgery using the inner cutting surface as an electrode. Inserting the surgical device includes inserting a surgical device that includes a third member coupled to the second member and including a return electrode.

According to another aspect, a surgical device includes a first member, a second member, and an electrical connector. The second member defines a lumen for receiving the first member, and the first member and the second member are configured to be movable with respect to each other to cut tissue. The electrical connector is physically and electrically coupled to the second member for electrically coupling the second member to a source of electricity. The surgical device includes a mechanism for holding a distal region of the first member in electrical contact with a distal region of the second member.

Described instruments allow tissue to be cut mechanically and coagulated with a single instrument, and the tissue can be cut and coagulated with the same surface of the instrument. Because the same surface can be used, the mechanical cutting and electrosurgery can also occur at approximately the same time. The instruments can perform other electrosurgery on tissue with or without also mechanically cutting tissue, and the electrosurgery can be monopolar or bipolar. In one instrument including an inner tube rotating within a second tube, electrical power is coupled to an electrode on the inner tube through contact at the distal end of the instrument between the inner and second tubes.

The details of one or more embodiments are set forth in the accompanying drawings and the description below. Other features will be apparent from the description, the drawings, and the claims.

DESCRIPTION OF DRAWINGS

FIG. 4A is a side view of the MDU of FIG. 2 with a distal portion shown in cross-section.

FIG. 4B is an enlarged view of a portion of the cross-section of FIG. 4A.

FIG. 6A is a side view of a middle tube assembly of the electroblade of FIG. 2.

FIG. 6B is a bottom view of a proximal portion of the middle tube assembly of FIG. 6A, taken along line 6B—6B in FIG. 6A.

FIG. 7A is a side view of an inner tube assembly of the electroblade of FIG. 2.

FIG. 7B is a cross-sectional view of a proximal portion of FIG. 7A.

FIG. 8A is an enlarged view of a distal portion of the electroblade of FIG. 2.

FIG. 8B is a top view of the distal portion of the electroblade, taken along line 8B—8B in FIG. 8A.

FIG. 8C is the top view of FIG. 8B without an inner tube.

FIG. 9A is a side view of the power cord of FIG. 3 showing a portion in cross-section that connects to the electroblade.

FIG. 9B is an enlarged view of a portion of the cross-section of FIG. 9A, shown in the same orientation as FIG. 9A and positioned so that the openings for the electroblade in FIGS. 9A and 9B are aligned.

FIG. 9C is a top view of a portion of FIG. 9B showing the electrical connection for an outer tube, taken along line 9C—9C in FIG. 9B, shown in a complimentary orientation relative to FIGS. 9A and 9B, and positioned on a line between the openings for the electroblade in FIGS. 9A and 9B.

FIG. 9D is a bottom view of a portion of FIG. 9B showing the electrical connection for a middle tube, taken along line 9D—9D in FIG. 9B, shown in the same orientation as FIG. 9C, and positioned on an extension of the line between the openings for the electroblade in FIGS. 9A and 9B.

DETAILED DESCRIPTION

Figure 1:
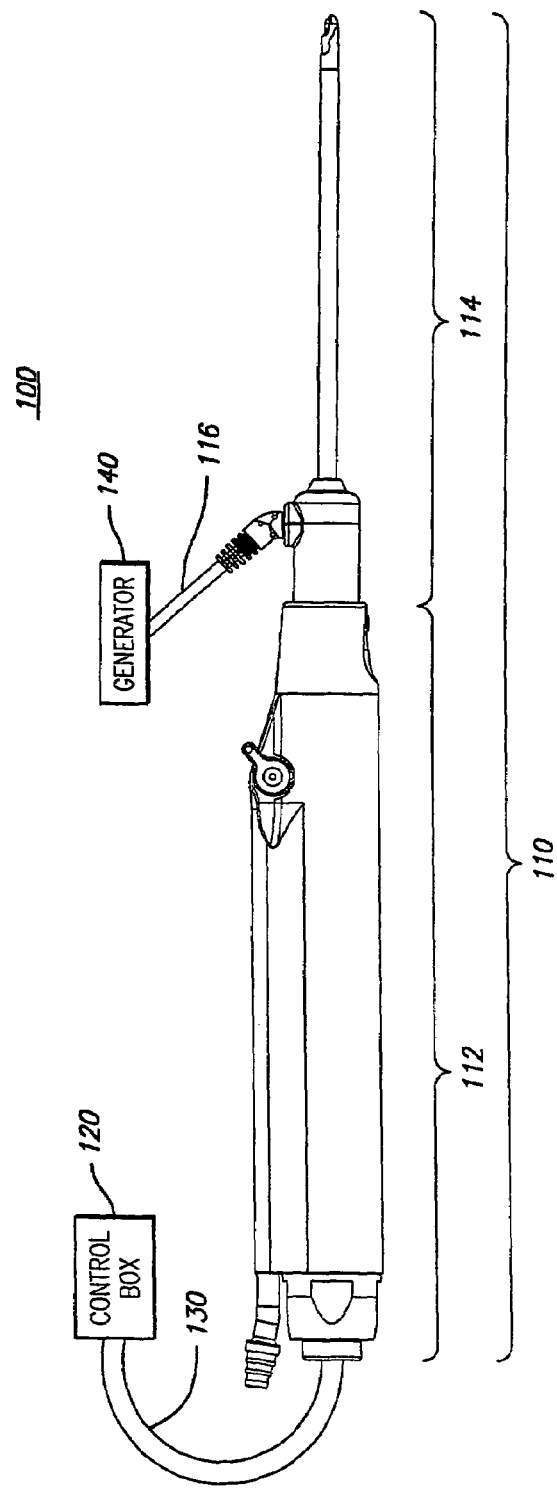
FIG. 1 is a side view of an embodiment of the surgical device, along with block diagrams for equipment connected to the surgical device.

Referring to FIG. 1, a surgical system 100 includes a surgical device 110 having a motor drive unit ("MDU") 112 mechanically coupled to an electroblade 114. Surgical device 110 also includes a RF bipolar power cord 116 electrically and mechanically coupled to electroblade 114 for supplying RF power to electroblade 114. Surgical system 100 further includes a control box 120 for supplying power to MDU 112 through a power cord 130, and a RF generator 140 for supplying RF power to electroblade 114 through RF power cord 116.

Figure 2:
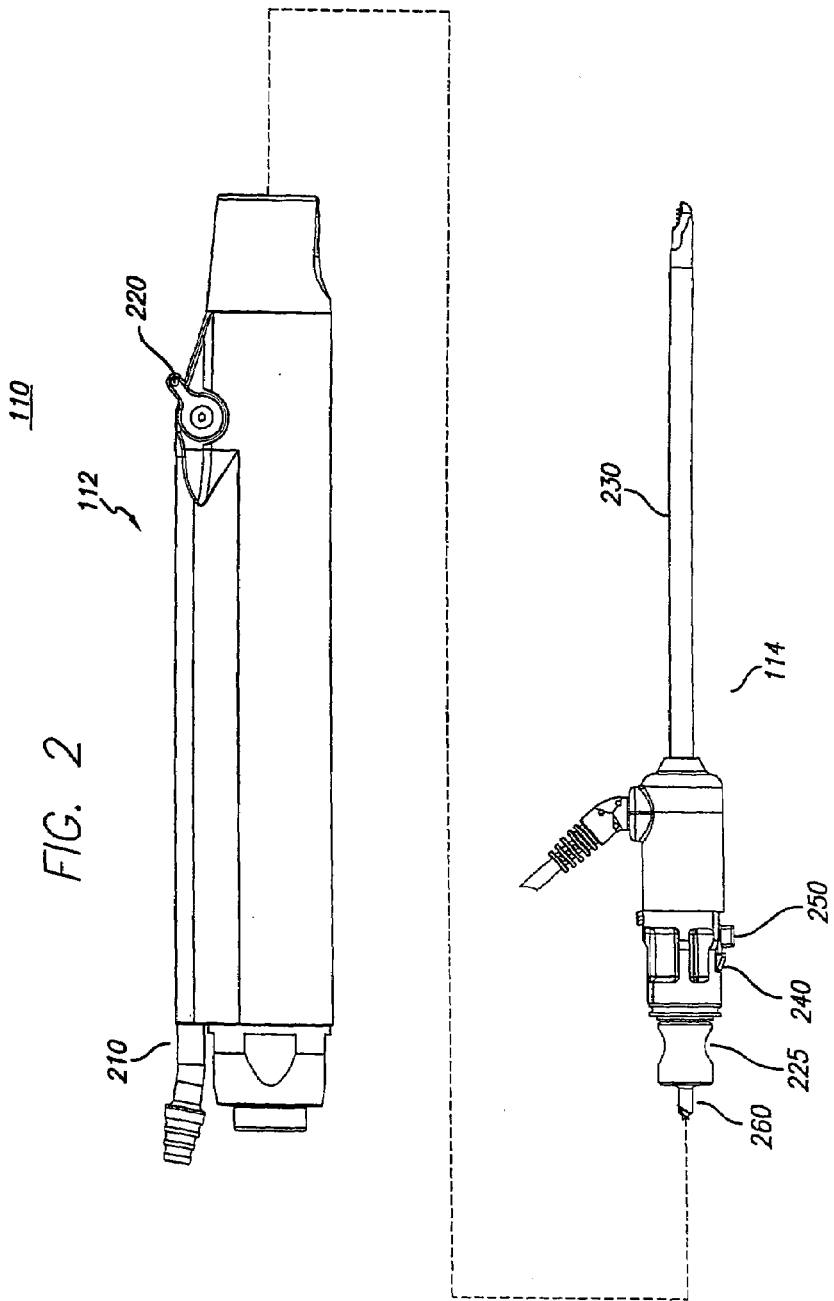
FIG. 2 is an exploded view of the surgical device of FIG. 1, separately showing an electroblade and a motor drive unit ("MDU").

Referring to FIG. 2, MDU 112 includes an aspiration tube 210 and an aspiration control 220. Aspiration tube 210 is coupled to a suction pump or other device to provide aspiration of tissue and fluid. Electroblade 114 includes an opening 225 that extends radially through electroblade 114 and communicates with aspiration tube 210 for aspiration. Electroblade 114 includes a distal portion 230 that is inserted into a patient's body to cut tissue mechanically and to perform electrosurgery.

Electroblade 114 includes a ridge 240 for connecting electroblade 114 to MDU 112. Ridge 240 is deflected radially inward when electroblade 114 is inserted into MDU 112 and ridge 240 retracts slightly (radially outward) when ridge 240 comes into alignment with a corresponding surface (not shown) in MDU 112. Ridge 240 thus engages the surface, attaching electroblade 114 to MDU 112. Electroblade 114 also includes a release 250 for releasing electroblade 114 from MDU 112. Pressing release 250 deflects ridge 240 radially inward disengaging ridge 240 from the groove, and allowing electroblade 114 to be withdrawn from MDU 112. Electroblade 114 further includes a tab 260 that is rotated by MDU 112. Commercial implementations of MDU 112 are available from Smith & Nephew, Inc., of Andover, Mass., in part numbers 7205354, 7205355, and 7205971.

Figure 3:
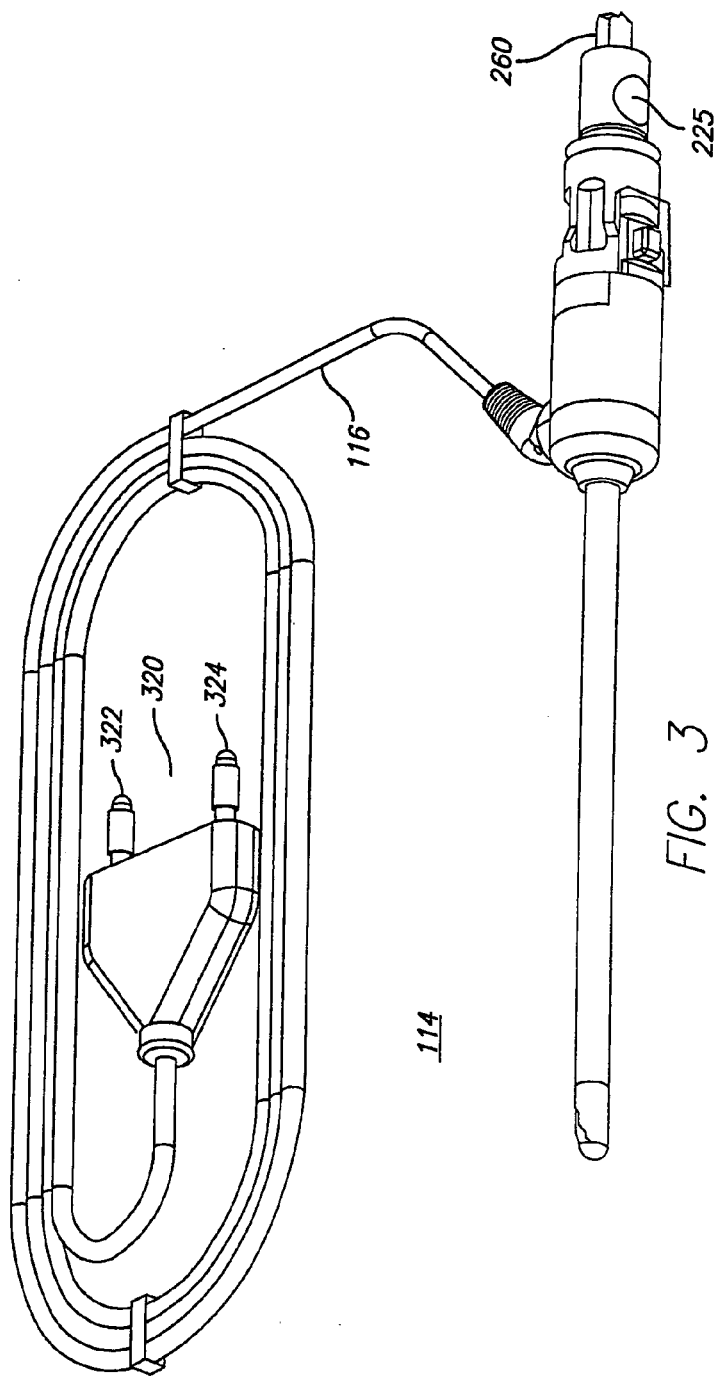
FIG. 3 is a perspective view of the electroblade of FIG. 2, also including a complete RF power cord.

Referring to FIG. 3, RF power cord 116 terminates at a free end with a connector 320. Connector 320 has two prongs 322 and 324 designed to connect to either a generator or a foot switch. Each prong connects to one of two separate conductors within RF power cord 116 to provide both a supply path and a return path for electroblade 114.

Figure 4C:
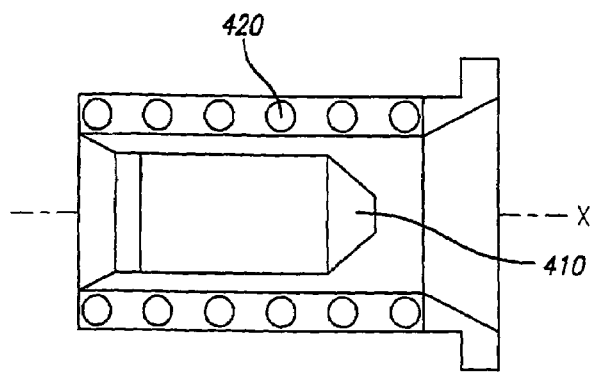
FIG. 4C is an enlarged view of a portion of FIG. 4B showing a tension device in greater detail.

Referring to FIGS. 4A–4C, MDU 112 includes a drive shaft terminating at a distal end in a pair of parallel prongs 410, only one of which is visible in cross-section. Tab 260 of electroblade 114 fits between prongs 410, and prongs 410 rotate tab 260 as the drive shaft is rotated. MDU 112 includes a tension device 420 that applies pressure to electroblade 114 when electroblade 114 is secured in MDU 112. As best shown in FIG. 4C, tension device 420 is, for example, a coil spring, that applies pressure generally along a longitudinal axis, X, of MDU 112 and electroblade 114. FIG. 4C shows the cross-section of the coils. Tension device 420 may also or alternatively include, for example, a compression spring (coil or otherwise); other types of springs, such as, for example, a leaf spring; an elastic device, such as, for example, a rubber grommet or a device made of an elastic plastic material; or a nozzle or other structure that provides fluid pressure, such as, for example, air pressure, rather than structural pressure.

Referring to FIG. 8A, a distal tip of electroblade 114 includes an inner tube 710, a middle tube 610, a middle tube insulating layer 620, an outer tube 510 having a distal exposed portion 540, and an outer tube insulating layer 520. The three tubes 510, 610, and 710 are concentric.

Figure 5:
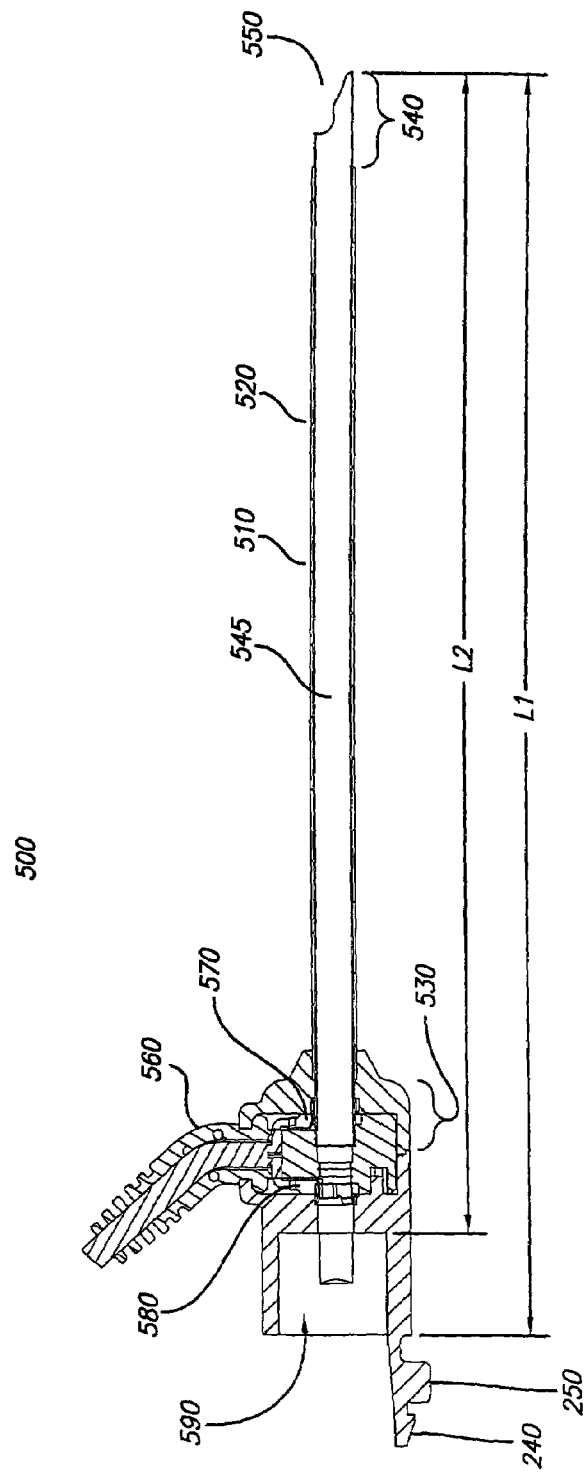
FIG. 5 is a cross-sectional side view of an outer tube assembly of the electroblade of FIG. 2B.

Referring to FIG. 5, an outer tube assembly 500 includes electrically conductive outer tube 510 covered by outer tube insulating layer 520 on all but a proximal portion 530 and distal portion 540. An electrode is defined by exposed distal portion 540 of outer tube 510, and this electrode is referred to as the return electrode as explained in detail below.

Outer tube 510 defines a lumen 545 and an opening 550 at a distal end in communication with lumen 545. Outer tube assembly 500 also includes an outer tube hub 560. Outer tube hub 560 includes an outer tube connector 570 for electrically connecting one of the conductors in RF power cord 116 to exposed proximal portion 530 of outer tube 510. Outer tube hub 560 also includes a middle tube connector 580 for electrically connecting the second conductor in RF power cord 116 to an exposed portion of middle tube 610. Connectors 570 and 580, and their connections, are further explained in the discussion of FIGS. 9A–9D. Outer tube hub 560 further includes a cavity 590 and, at a portion extending proximal to cavity 590, release 250 and ridge 240 (described above). Note that outer tube 510 does not extend proximally of exposed proximal portion 530, and that no tube is located in cavity 590 in FIG. 5; rather, cavity 590 includes markings on the interior wall of cavity 590 that resemble the outline of a tube.

Outer tube assembly 500 has an approximate length for dimension L1 of, for example, 6.4 inches, and an approximate length for dimension L2 of, for example, 5.9 inches. These dimensions are not critical to operation and can vary depending on, for example, the location of the body tissue on which surgical device 110 is to operate.

Referring to FIGS. 6A, 6B, 8A, and 8B, a middle tube assembly 600 includes electrically conductive middle tube 610 covered by middle tube insulating layer 620 on all but a proximal portion 630 and a distal portion (labeled as 610 in FIG. 8A). Middle tube 610 defines a lumen 635 and an opening 640 at a distal end in communication with lumen 635. Opening 640 is bounded by a sharp edge 820 for cutting (FIG. 8B) that is part of the exposed distal portion (610 in FIG. 8A) not covered by insulating layer 620. Middle tube 610 also includes a distal portion 645 that is rounded, a straight portion 646, and an inside surface 647 (FIG. 6B). A tangent line 648 shows the demarcation between distal rounded portion 645 and straight portion 646. Middle tube assembly 600 includes a middle tube hub 650 including a distal portion 652 and a proximal portion 654. Middle tube assembly 600 also includes a cavity 656 in a proximal end 660.

Middle tube assembly 600 is fixed to outer tube assembly 500, such that both assemblies 500 and 600 are stationary. That is, neither assembly 500 or 600 is rotated by MDU 112. Middle tube 610 and insulating layer 620 are positioned inside of outer tube 510 and protrude past distal opening 550 of outer tube 510, as shown in FIG. 2B, to electrically isolate outer tube 510 from middle tube 610. Middle tube connector 580 contacts exposed portion 630 of middle tube 610 to provide an electrical connection to middle tube 610. Distal portion 652 of middle tube hub 650 fits inside cavity 590 of outer tube hub 560. Proximal portion 654 abuts cavity 590 and includes a cut-out 670 (FIG. 6B) that surrounds ridge 240 and release 250 as shown in FIG. 2B.

Middle tube assembly 600 has an approximate length for dimension L3 of, for example, 7.5 inches, and an approximate length for dimension L4 of, for example, 6.0 inches. These dimensions are not critical to operation and can vary depending on, for example, the location of the body tissue on which surgical device 110 is to operate.

Referring to FIGS. 7A and 7B, an inner tube assembly 700 includes electrically conductive inner tube 710 and an inner tube hub 720 having a distal portion 722 and a proximal portion 724. Inner tube 710 is not covered by an insulating layer, and a distal portion serves as an electrode as described in detail below. Inner tube 710 defines an aspiration lumen 728 and includes an opening 730 in communication with aspiration lumen 728. Opening 730 is bounded by a sharp edge (labeled 810 in FIG. 8B) for cutting. A proximal end 740 of aspiration lumen 728 is in communication with opening 225, as shown in FIG. 7B.

Inner tube assembly 700 can be rotated by MDU 112 while middle tube assembly 600 and outer tube assembly 500 remain stationary. Inner tube 710 is positioned inside of middle tube 610. As explained earlier, tension device 420 applies longitudinal pressure. The pressure applied by tension device 420 causes a distal rounded portion 750 of an outer surface 760 of inner tube 710 to abut distal portion 645 of inner surface 647 of middle tube 610 (FIG. 8B), thereby making electrical contact. Distal portion 722 of inner tube hub 720 fits inside of cavity 656 in proximal end 660 of middle tube assembly 600. Proximal portion 724 is exposed, as seen in FIG. 2B. In addition, or alternatively, electrical contact can be made between outer surface 760 of a straight portion 770 of inner tube 710 and inner surface 647 of straight portion 646 of middle tube 610. Note that a tangent line 780 (see FIGS. 7A and 8A) shows the demarcation between distal rounded portion 750 and straight portion 770. Such contact between straight portions 646 and 770 may be only incidental, not providing a reliable electrical connection, such that the distal tip connection provides the primary electrical connection between middle tube 610 and inner tube 710.

Inner tube assembly 700 has an approximate length for dimension L5 of, for example, 7.0 inches. This dimension is not critical to operation and can vary depending on, for example, the location of the body tissue on which surgical device 110 is to operate.

Referring again to FIG. 8A, middle tube 610 and middle tube insulating layer 620 extend past uninsulated distal portion 540 of outer tube 510 to provide electrical isolation between middle tube 610 and outer tube 510. Inner tube 710 extends into opening 640 in middle tube 610 to expose a portion of inner tube 710 for use as an electrode and a cutting instrument. Opening 730 in inner tube 710 is shown facing up (in FIG. 8A), in the same direction as opening 640. Because the entire part of inner tube 710 that is visible in opening 640 has had a portion removed to form opening 730, inner tube 710 appears to have a disproportionately small diameter compared to the diameter of middle tube 610.

Referring to FIGS. 8B and 8C, opening 730 in inner tube 710 is partially bounded by an uninsulated cutting edge 810 of inner tube 710. Edge 810 bounds the two sides and a distal perimeter 815 of opening 730. Opening 640 in middle tube 610 is completely bounded by the uninsulated oval-shaped cutting edge 820 of middle tube 610. Proximal to edge 820 is a crescent-shaped exposed portion 825 of middle tube 610, and surrounding both edge 820 and the crescent-shaped exposed portion of middle tube 610 is an oval-shaped beveled edge 830 of middle tube insulating layer 620. FIG. 8C provides a more isolated view of edges 820 and 830 and crescent-shaped exposed portion 825. In summary, the uninsulated exposed surfaces include edge 810 of inner tube 710 which provides an edge for mechanical cutting and electrosurgery, edge 820 of middle tube 610 which provides an edge for mechanical cutting, and crescent-shaped exposed portion 825. Alternatively, no portion of middle tube 610 between edge 830 and edge 820 need be uninsulated. For example, middle tube insulating layer 620 can cover all of the distal portion of middle tube 610 except for approximately 0.02 inches around opening 640 used for edge 820. As stated above, edge 820 is uninsulated to allow edge 820 to be unimpeded during mechanical cutting. Because edge 820 is uninsulated, edge 820 also serves as part of an electrode, however such use is incidental and typically forms a small part of the electrode as explained in more detail below.

As inner tube assembly 700 (FIG. 7) is rotated by prongs 410 (FIG. 4) engaging tab 260 (FIGS. 2B and 3), edge 820 of middle tube 610 (FIG. 8B) works cooperatively with edge 810 of inner tube 710 (FIG. 8B) in a scissors-like cutting action to cut tissue disposed between edges 820 and 810. Tissue can be drawn between edges 820 and 810 with the aid of aspiration through opening 640 in middle tube 610 and opening 730 in inner tube 710.

Inner tube assembly 700 can be rotated continuously or intermittently in either a forward or a reverse direction, or oscillated in both directions. The direction of rotation, the speed of rotation, the timing of oscillations between the two directions, the torque control, and other variables can be varied as appropriate for a given application. Inner tube 710 can be locked in one position by MDU 112 to prevent rotation of inner tube 710, and a locking position can be selected. These and other variables can be controlled at MDU 112 using, for example, hand controls, such as, for example, pushbuttons. Variables also can be controlled at, for example, control box 120 or a hand switch or foot switch positioned between control box 120 and MDU 112.

As mentioned earlier, a first electrode is defined by the exposed distal portions of inner tube 710 and, incidentally, middle tube 610 that contact tissue. These exposed portions include a variable portion of inner tube 710 that is visible through opening 640, and that part of middle tube 610 forming edge 820 and the crescent-shaped exposed portion 825 proximal to edge 820. The portion of inner tube 710 visible through opening 640 is variable because inner tube 710 can be rotated. The first electrode has a proximal portion 840, a middle portion 850, and a distal portion 860, as shown in FIGS. 8A and 8B.

A second electrode is defined by exposed distal portion 540 of outer tube 510. A circuit is completed between the two electrodes by immersing both electrodes in a conductive environment. A conductive environment can be produced, for example, from a 9% normal saline solution, or from Ringers lactate, a physiologically compatible conductive solution. The conductive solution also can serve as an irrigant and to distend a body cavity. In practice, the circuit typically also extends through tissue that is positioned adjacent the first electrode.

The second electrode has a surface area that is approximately five times larger than the surface area of the first electrode, and the greater surface area allows for a lower current density at the second electrode than at the first electrode. Specifically, when inner tube 710 is fully closed, the surface area of the second electrode is five times larger than the exposed surface area of inner tube 710. The ratio is larger when inner tube 710 is in another position, such as, for example, only three-fourths closed. The ratio is minimally affected when the exposed surface area of middle tube 610 is considered as part of the first electrode.

The current density at the first electrode is further increased at sharp edge 810 of inner tube 710. The higher current density at the first electrode generally gives rise to a tissue effect being seen on tissue adjacent or near the first electrode and not on tissue adjacent or near the second electrode. Tissue effects include, for example, coagulation and shrinkage and the term electrosurgery encompasses electrical surgery that achieves these or other tissue effects.

Electrical energy can be applied to tissue using one of the first or second electrodes, and electrical energy can return to electroblade 114 through the other of the two electrodes. Accordingly, either electrode can act as an active electrode or as a return electrode. However, for simplicity, the first electrode is referred to as the active electrode and the second electrode is referred to as the return electrode.

Referring to FIG. 9A, one end of RF power cord 116 includes a connector 910 that provides electrical connections to middle tube 610 and outer tube 510, and ultimately to the active and return electrodes. Connector 910 forms part of outer tube hub 560 and, along with outer tube hub 560, is fixed to outer tube 510 and middle tube 610.

Referring to FIG. 9B, connector 910 includes outer tube connector 570, middle tube connector 580, and a housing 920. Outer tube connector 570 includes an upper tab 932 and three lower tabs 934 (see also FIG. 9C). Similarly, middle tube connector 580 includes an upper tab 936 and three lower tabs 938 (see also FIG. 9D). Housing 920 defines a conductor channel 940 through which two RF conductors 942 and 944 are passed from power cord 116 to connectors 570 and 580. Conductor 942 couples to tab 932 of connector 570, and conductor 944 couples to tab 936 of connector 580 to provide power to tabs 932 and 936.

Housing 920 also defines a tube channel 950, through which one or more tubes and/or insulating layers are fixed during assembly. In an assembled electroblade, middle tube 610, middle tube insulating layer 620, and outer tube 510 each are fixed within tube channel 950. Tube channel 950 has varying diameters to accommodate the various tubes and insulating layers.

Referring to FIG. 9C, outer tube connector 570 is generally described as a three-sided connector and/or a three-point connector. Connector 570 is self-centering on outer tube 510. That is, because connector 570 has three tabs 934 distributed around outer tube 510 that contact tube 510, connector 570 tends to position itself such that outer tube 510 is centered within connector 570.

Referring to FIG. 9D, middle tube connector 580 is similar to connector 570. The diameter of tube channel 950 is smaller at the opening surrounded by connector 580 than at the opening surrounded by connector 570 because the diameter of middle tube 610 is smaller than the diameter of outer tube 510.

RF power is applied to electroblade 114 using generator 140 and RF power cord 116 (FIG. 1). As explained earlier, connector 320 (FIG. 3) is connected to generator 140 directly or through a foot switch. One prong 322 (or 324) electrically connects both middle tube 610 and inner tube 710 to the generator using middle tube connector 580 (FIG. 9D). RF power is transferred from middle tube 610 to inner tube 710 principally through distal portions 645 and 750 of tubes 610 and 710, respectively (FIGS. 5, 8A, and 8B). The other prong 324 (or 322) electrically connects outer tube 510 to the generator using outer tube connector 570 (FIGS. 5 and 9C).

By applying RF power during a mechanical cutting operation, the RF power can be used, for example, to coagulate tissue as the tissue is cut mechanically. RF power also can be applied when no mechanical cutting operation is taking place in order, for example, to coagulate previously cut tissue. If no mechanical cutting is desired, inner tube 710 can be locked in a particular position, such as, for example, a position that "closes" or obscures three-fourths of opening 640 in middle tube 610. A three-fourths-closed position exposes additional surface area of inner tube 710 to provide a greater area, for example, for coagulation, and still provides a one-fourth opening for aspiration. Inner tube 710 can be locked by setting MDU 112 so that prongs 410 do not allow rotation.

Electroblade 114 is designed to coagulate tissue at the active electrode, and not to ablate tissue under normal operating conditions which are discussed below. The relative surface areas of the active and return electrodes, and the use of formations (for example, edges) both promote coagulation by controlling current density, as discussed above. The inter-electrode distance has also been designed to facilitate coagulation. The return electrode of electroblade 114 is closest to the active electrode at approximately the middle 850 of the active electrode, and the return electrode is farthest from the active electrode at the proximal end 840 of the active electrode. Such spacing has been found to provide a current density appropriate for coagulation.

Design parameters and/or operating conditions can be varied to provide coagulation capability in different embodiments. For example, design parameters such as the relative surface areas of the two electrodes, the types of formations on the electrodes (for example, edges), and the distance between the active and return electrodes can be varied to affect current densities. The current density tends to be greatest where the inter-electrode distance is smallest, and where there are formations, such as, for example, edges, that concentrate current. As a further example, operating conditions such as the power level for coagulation can be varied depending on, for example, the surface area of the electrodes and the amount of tissue being cut.

The RF power that is applied can be controlled using, for example, generator 140, a foot switch or other foot-operated control, and a hand switch or other hand-operated control including controls integrally mounted in MDU 112 or electroblade 114. RF power controls can be provided for parameters, such as, for example, the type and/or shape of the RF waveform, the level of power, the direct current ("DC") bias, and the duration of the RF power. RF control also can include temperature detection and feedback using, for example, a thermocouple or thermistor that is integrally mounted in electroblade 114. Frequencies outside of the RF band also can be used.

Figure 10:
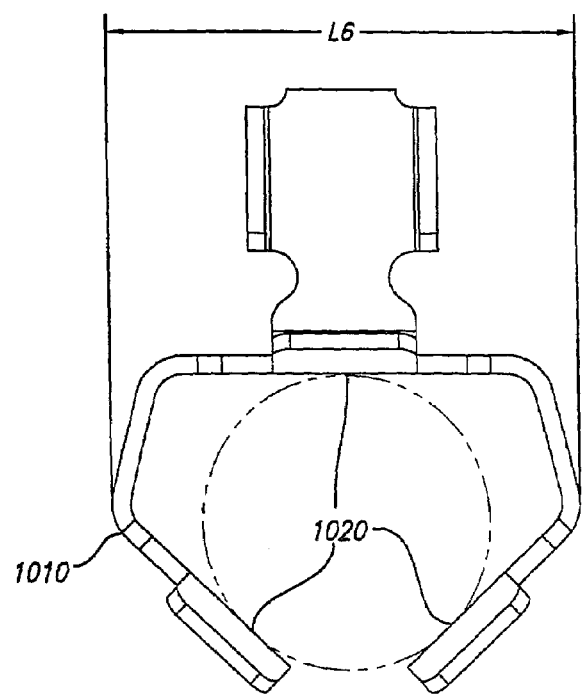
FIG. 10 is a top view of an alternate embodiment of the electrical connections of FIGS. 9C and 9D.

Referring to FIG. 10, in an alternative embodiment of a connector for connecting electrical power from a conductor in cable 116 to a tube, such as, for example, tube 510, 610, or 710, a connector 1010 includes three contacts 1020 and is generally described as a five-sided connector and/or a three-point connector (as opposed to the three-sided connector of FIGS. 9A–9D). The use of five sides, compared to three, has the effect of flattening the curves associated with connectors 570 and 580 and allowing a reduction of the dimension L6, and a consequent reduction of the required size of connector 910 and outer tube hub 560. As with connectors 570 and 580, connector 1010 is self-centering on, slidable along, and rotatable around either outer tube 510 or middle tube 610. Connectors can have various numbers of sides and/or contacts depending on, for example, the desired dimensions of the connector or the desired current density at any given contact.

Connector 1010 has an approximate length for dimension L6 of, for example, 0.26 inches. This dimension is not critical to operation and can vary depending on, for example, the diameter of the concentric tubes 510, 610, and 710.

Figure 11A:
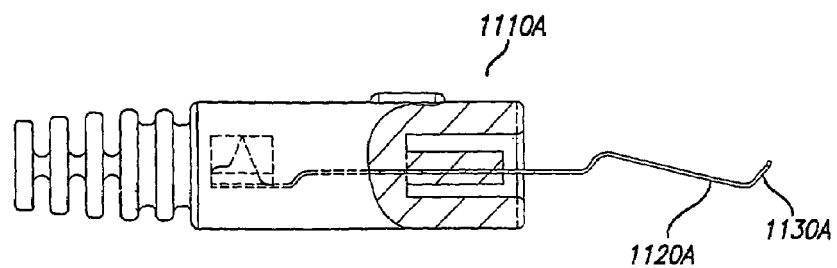
FIG. 11A shows an alternate embodiment of a connector for providing electrical connections to an electroblade.

Referring to FIG. 11A, in an alternative embodiment of a connector for connecting electrical power from a conductor in cable 116 to a tube, such as, for example, tube 510, 610, or 710, a connector 1110A provides an electrical connection to electroblade 114. Connector 1110A includes a conductor 1120A in the form of a flexible metal conductor that operates as a leaf spring to make contact at a distal portion 1130A with a tube.

Figure 11B:
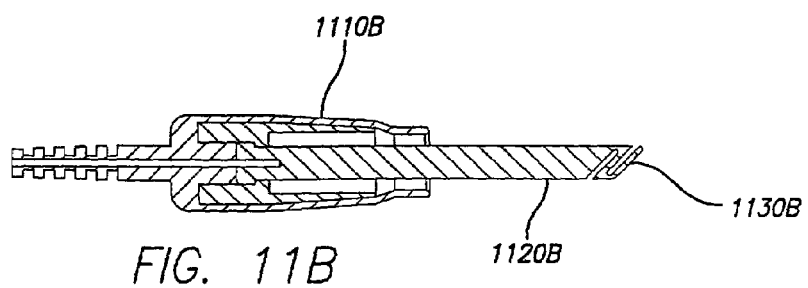
FIG. 11B shows another alternate embodiment of a connector for providing electrical connections to an electroblade.

Referring to FIG. 11B, in another alternative embodiment of a connector for connecting electrical power from a conductor in cable 116 to a tube, such as, for example, tube 510, 610, or 710, a connector 1110B includes a conductor 1120B in the form of a flexible metal conductor that operates as a compression spring to make contact at a distal portion 1130B with a tube.

Figure 11C:
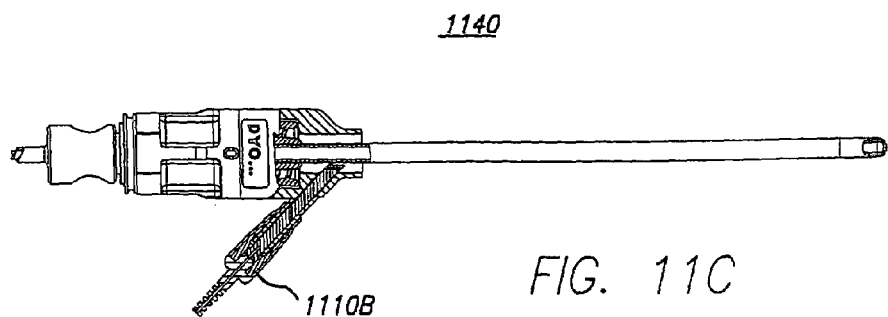
FIG. 11C shows an alternate embodiment of an electroblade using the electrical connector of FIG. 11B.

Referring to FIG. 11C, a device 1140 shows connector 1110B coupling to a tube at an angle such that distal portion 1130B makes a reliable contact with the tube. Such contact can be with a stationary tube, such as, for example, outer tube 510 or middle tube 610, or with a moving tube, such as, for example, inner tube 710. Connectors 1110A and 1110B can include two or more conductors 1120A and 1120B, respectively, to provide connections, for example, for an active electrode and a return electrode. Although contact can be made with a moving tube along a straight portion of the tube, such contact would not enjoy the benefits and advantages of providing electrical contact at a distal end of the tubes as described herein.

Figure 12:
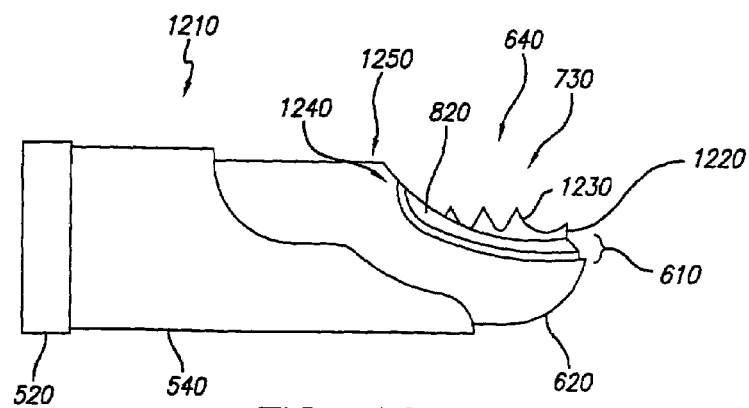
FIG. 12 is an enlarged view of a distal portion of an alternate embodiment of the electroblade of FIG. 2 having a serrated cutting surface.

Referring to FIG. 12, in an alternative embodiment of inner tube 710, a distal portion 1210 of an electroblade similar to electroblade 114 includes an inner tube 1220 with a serrated, or toothed, edge 1230 surrounding opening 730. Serrated edge 1230 is particularly useful in cutting tissue that is described variously as being ligamentous, banded, or rubbery. Other types of edges can be employed to surround opening 730, depending, for example, on the particular application. Due to the angle of the view, a portion 1240 of middle tube insulating layer 620 appears to cover part of opening 640, however, opening 640 does continue to a top 1250 of middle tube 610, as in FIGS. 6A, 8A, and 13 (below).

Figure 13:
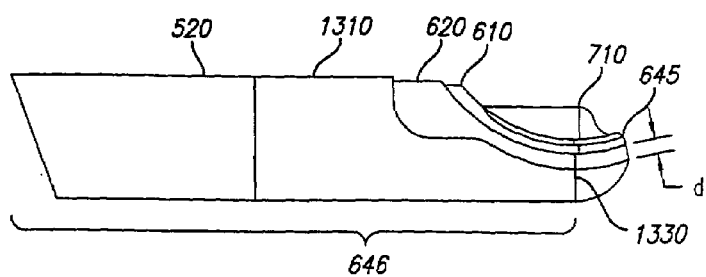
FIG. 13 is an enlarged view of a distal portion of another alternate embodiment of the electroblade of FIG. 2 having a closed-ended return electrode.

Referring to FIG. 13, in an alternate embodiment of outer tube 510, a distal portion 1305 of an electroblade similar to electroblade 114 includes a closed-ended outer tube 1310 that extends distally past a straight portion 646 of middle tube 610 and curves around to partially cover distal rounded portion 645 of middle tube 610. Closed-ended outer tube 1310 provides a smaller inter-electrode distance, d, at distal portion 860 of middle tube 610 than does outer tube 510 (compare FIG. 8A). The smaller inter-electrode distance is a result of a distal rounded portion 1330 of outer tube 1310. Note that distance "d" is shown for simplicity as a linear measurement in FIG. 13, however, the true distance traversed can be a curved line. Although outer tube 510 and closed-ended outer tube 1310 can be used in various configurations of electroblade 114, closed-ended outer tube 1310 has found particular application in embodiments using larger diameter concentric tubes. For example, outer tube 510 is particularly applicable where the diameter of the outer tube is approximately 4.5 millimeters, and closed-ended outer tube 1310 is particularly applicable where the diameter of the outer tube is approximately 5.5 millimeters. The closer inter-electrode distance at distal portion 860 is useful in the 5.5 millimeter implementation to provide a higher current density at distal portion 860 and, as a result, provide for coagulation at distal portion 860 without increasing power substantially. Variations of closed-ended outer tube 1310 can cover more or less of middle tube 610, including covering more or less of rounded distal portion 645. Such variations will affect the inter-electrode distance at different locations along the electrodes and, as a result, will affect the current density at those locations.

Figure 14:
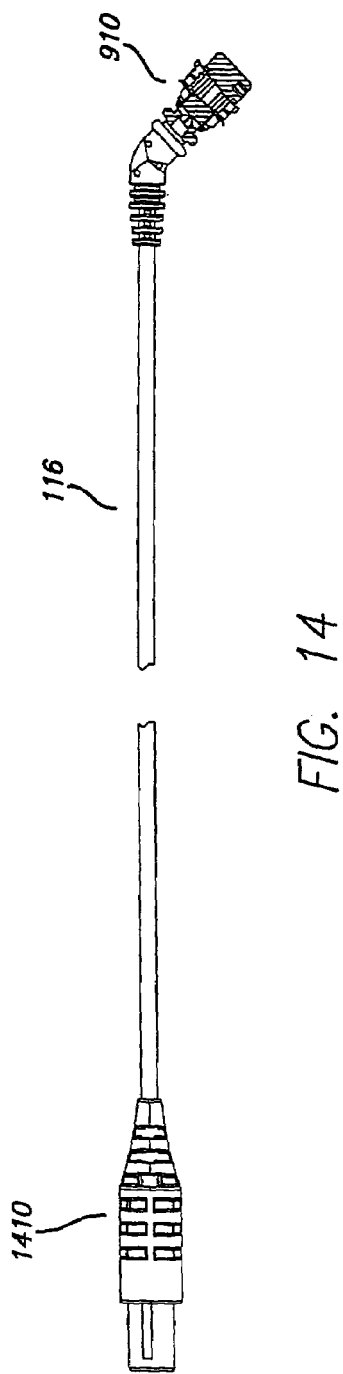
FIG. 14 is a side view of an alternate embodiment of the power cord of FIG. 9A showing a different generator connector.

Referring to FIG. 14, RF power cord 116 can include an integral connector 1410 for connecting power cord 116 to a Vulcan Generator produced by Oratec Interventions, Inc. of Menlo Park, Calif., now owned by Smith & Nephew, Inc. Vulcan connector 1410 includes a resistor (not shown) that allows the Vulcan Generator to identify the attached instrument as an electroblade and to provide a pre-programmed output to the electroblade.

Referring again generally to FIG. 1, control box 120 is, for example, the Dyonics® Power Shaver system or the Dyonics® EP-18 Shaver System supplied by Smith & Nephew, Inc. of Andover, Mass. Generator 140 is a commercially available generator such as, for example, a Vulcan Generator or a Valleylab Electrosurgical Generator Force FXTM, Force FXTM-C, or ForceTM 2, supplied by Valleylab, a division of Tyco Healthcare Group L.P., of Boulder, Colo. Various embodiments are easily integrated into a standard operating room because (i) the mechanical and RF operations, as well as aspiration, are performed with the same instrument, (ii) a standard operating room generator can be used, and (iii) no grounding pad is necessary.

Typical generator settings are between zero and seventy watts for coagulation, with the generator allowing settings up to one-hundred watts. Typical settings for use with an inner tube and cutting surface that are stationary include minimum coagulation settings of between twenty and forty watts, and recommended coagulation settings of between thirty and fifty watts. Such settings are used, for example, when inner tube 710 is locked in a position closing off three-fourths of opening 640 in middle tube 610. If the inner tube is moving, thus providing simultaneous mechanical cutting and RF electrosurgery, typical minimum power settings for coagulation range from thirty to fifty watts, and recommended coagulation power settings range from fifty to seventy watts.

The generator provides, for example, waveforms having an open circuit maximum peak-to-peak voltage of 800 volts with no load. Typical settings on one of the Valleylab generators include both 320 volts peak-to-peak and 750 volts peak-to-peak, with a maximum peak-to-peak voltage of 1000 volts. Frequency settings typically range from approximately 470–510 kilohertz ("kHz") for a sinusoidal wave, with a nominal setting of 500 kHz.

The electroblade is sized to accommodate the desired application. For example, for use in a shoulder the electroblade is sized differently from one for use in a prostate. Applications include, for example, use in a shoulder, a knee, and other joints, as well as use in natural orifices such as, for example, a uterus, a urethra, a nasal cavity, and a mouth.

The electroblade assembly is designed as, for example, a single-use, sterile, disposable assembly. Alternatively, the electroblade is a multiple-use assembly that can be cleaned and re-sterilized. Single-use assemblies obviate the need to clean between the tubes and may be made using materials, such as, for example, plastics, that cannot be steam re-sterilized, thereby preventing multiple uses. Conversely, device components, such as, for example, outer tube 510 and middle tube 610, need not be fixed to outer tube hub 560, thus allowing such components to be more amenable to cleaning.

Referring again to FIG. 2B, electroblade 114 can be attached to MDU 112 using various other structures, for example, threaded connections and pressure-fit connections. Various embodiments of MDU 112 include motor drive units manufactured by Smith & Nephew, Inc., of Andover, Mass., such as, for example, part numbers 7205354, 7205355, and 7205971.

Referring again generally to FIGS. 5–7, outer tube connector 570 and middle tube connector 580 can clip onto outer tube 510 and middle tube 610, respectively, or slide over one of the ends of tube 510 or 610. The outer tube connector and the middle tube connector can contact outer tube 510 and middle tube 610, respectively, in various ways including, for example, by using an electrically conductive clip, an electrically conductive leaf spring, or a solder connection.

Outer tube insulating layer 520 and middle tube insulating layer 620 are, for example, heat shrinkable tubing that is placed over outer tube 510 or middle tube 610, respectively, then shrunk and trimmed to desired dimensions, or a halar coating having a thickness of, for example, 0.009 inches or more. Other embodiments may use materials that are, for example, painted, sprayed, or deposited on one or more surfaces (for example, interior and exterior) of a tube. Materials include, for example, ceramics, plastics, and silicone. Other embodiments may use one or more insulating layers that are not secured to a tube. Non-secured insulating layers may be made from plastic or ceramic, for example. Further, middle tube insulating layer 620 may be on the inner surface of outer tube 710 rather than, or in addition to, middle tube 610.

The various tubes and insulating layers can be selected to facilitate energy transfer. The inner and middle tubes can be coated, for example, to expose only the edge of the cutting surfaces and the bearing surfaces, thereby focusing energy and facilitating electrosurgery. Further, the bearing surfaces of tubes, such as, for example, the interior and exterior of the tubes, need not be exposed and can be, for example, coated with silicone. The tubes themselves need not be metal, or entirely conductive. For example, the inner tube can be plastic with a conductor at a distal end to make electrical contact with the middle tube and to provide conductive cutting edges where contact is made with tissue. Such an embodiment reduces metal exposed to any saline fluid and concentrates energy. As another example, a plastic middle tube can be used having a conductive strip, metal or otherwise, between the distal end and the proximal connection to RF power cord 116. As a further example, an inner tube can be non-conductive, although it still may have a cutting edge, and the active electrode is provided by the middle tube having a conductive cutting edge. As yet another example, one embodiment does not use a middle tube, but instead uses a brush mechanism to make electrical contact between a rotating inner tube and a connector from an RF power cord. Such a brush embodiment also may include a middle tube that is not conductive and that has a cutting edge that mates with a cutting edge on the inner tube.

The electroblade can be a monopolar instrument without an outer tube. Whether monopolar or bipolar, embodiments may provide electrosurgery at the surface that provides mechanical cutting or at another surface.

As described earlier, electrical contact between the inner and middle tubes is reliably maintained using a spring or other tensioning device, such as, for example, a coil spring, a leaf spring, or a rubber grommet or other elastic material that is coated, if desired, with a lubricant. Regardless of the tension device, physical contact between inner tube 710 and middle tube 610 can occur across various surface areas and/or points of contact. For example, the location and extent of contact can depend on the shapes of the distal ends of tubes 610 and 710 (for example, flat or rounded, and, if rounded, the relative radii of curvature) and the size and location of openings 640 and 730.

Electrical contact between tubes 610 and 710 can be provided by, for example, (i) providing physical contact along some part of the longitudinally extending walls of tubes 610 and 710, (ii) designing and machining tubes 610 and 710 with small (tight) tolerances so that an electrical connection is maintained during rotation without the use of an additional tensioning device, (iii) having a conductive solution fill some of the space between tubes 610 and 710, or (iv) using a conventional brush and slip ring mechanism.

The various references to a brush being used to provide electrical contact between middle tube 610 and inner tube 710 do not suggest that a brush would enjoy all of the benefits of the present invention. Rather, a brush is mentioned to provide another example of a manner of providing electrical contact. A brush, and other known techniques of providing electrical contact, may be used in conjunction with advantageous features disclosed herein.

Other motions can be used to perform mechanical cutting, such as, for example, a reciprocating motion. Electrical contact in a reciprocating embodiment can be maintained by using, for example, tight tolerances, a flexible wire, or a brush and slip-ring mechanism.

A variety of cutting surfaces can provide mechanical cutting. Such surfaces include, for example, blades that are curved, burred, straight, serrated, or miniature. Mechanical cutting is typically achieved with speeds in the thousands of cycles (for example, revolutions or reciprocations) per minute. Further, embodiments need not have cutting surfaces on both inner tube 710 and middle tube 610, for example, only inner tube 710 includes a cutting surface and opening 640 in middle tube 610 does not have a sharp edge.

Figure 15:
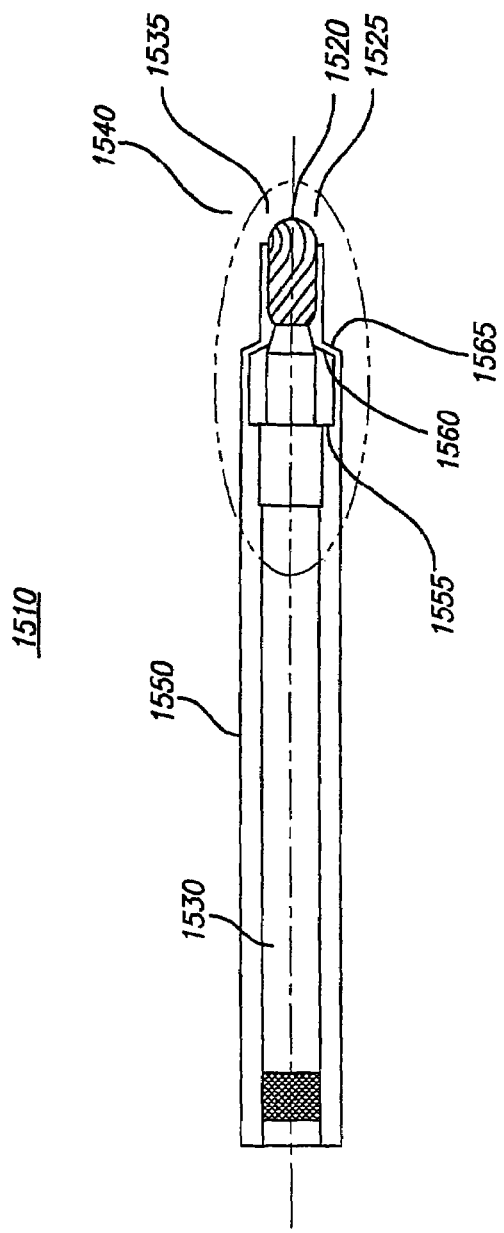
FIG. 15 is a side view of an alternate embodiment of an electroblade including a burr.

Referring to FIG. 15, an electroblade distal portion 1510 includes a burr 1520 at a distal end 1525 of an inner tube or shaft 1530. Burr 1520 protrudes from a lumen opening 1535 at a distal end 1540 of a middle tube 1550. Proximal to burr 1520, inner tube 1530 includes a shoulder 1555 with a tapered surface 1560. Middle tube 1550 includes a tapered surface 1565 configured to contact tapered surface 1555 of inner tub 1530. MDU 112 can be used to apply longitudinal pressure on inner tube 1530 so that tapered surfaces 1555 and 1565 contact each other and transfer electrical power from middle tube 1550 to inner tube 1530, and eventually to burr 1520. As FIG. 15 shows, cutting surfaces, such as, for example, a burr, can be provided on an inner tube that has a distal shoulder portion that engages the middle tube under the pressure of a tension device and provides electrical contact with the middle tube and electrical energy to the cutting surface.

A resistive element can be used to provide heat energy for coagulation. Embodiments may be designed to operate in a non-conductive environment with both electrodes configured to touch the tissue to be treated.

A number of embodiments have been described. Nevertheless, it will be understood that various modifications may be made. For example, features of the above-described embodiments generally may be combined in ways not discussed and other features or variations not discussed also may be used. Accordingly, other embodiments are within the scope of the following claims.

What is claimed is:

1. A surgical device comprising:
    a first member that defines an inner lumen operable as an aspiration lumen;
    a second member defining a lumen for receiving the first member, the first member and second member being configured to be movable with respect to each other to cut tissue;
    an electrical connector physically and electrically coupled to the second member for electrically coupling the second member to a source of electricity; and
    a tension device for holding a distal region of the first member in electrical contact with a distal region of the second member.

2. The surgical device of claim 1 wherein the electrical connector is self-centering on the second member.

3. The surgical device of claim 1 wherein the second member comprises a tube and the electrical connector comprises a three-point connector that is self-centering on the tube.

4. The surgical device of claim 1 further comprising a third member physically coupled to the second member and electrically isolated from the distal region of the first member.

5. The surgical device of claim 4 wherein:
the surgical device further comprises a first electrode in electrical contact with the distal region of the first member,
the third member comprises a second electrode, and
the surgical device is operable as a bipolar electrosurgical device using the first electrode and the second electrode.

6. The surgical device of claim 5 wherein:
the first member comprises a first tube,
the second member comprises a second tube, the second tube being cylindrical, and
the third member comprises a third tube disposed about the second tube.

7. The surgical device of claim 5 wherein an exposed surface area of the second electrode is at least approximately five times larger than an exposed surface area of the first electrode.

8. The surgical device of claim 1 further comprising an electrode in electrical contact with the distal region of the first member, wherein the surgical device is operable as a monopolar electrosurgical device using the electrode.

9. The surgical device of claim 8 wherein the electrode is part of the first member.

10. The surgical device of claim 1 wherein the tension device holds a tip of the first member in electrical contact with a tip of the second member.

11. The surgical device of claim 1 wherein the first member defines a longitudinal axis and the tension device applies tension along the longitudinal axis of the first member.

12. The surgical device of claim 1 wherein the tension device comprises a spring.

13. The surgical device of claim 1 further comprising a lock physically coupled to the second member for coupling the second member to the tension device.

14. The surgical device of claim 1 further comprising a drive unit coupled to the first member for moving the first member relative to the second member, wherein the second member is fixed with respect to the drive unit.

15. The surgical device of claim 1 wherein the first member comprises an electrically conductive cutting surface configured to cut tissue mechanically and to perform electrosurgery.

16. The surgical device of claim 15 wherein the cutting surface comprises a blade.

17. The surgical device of claim 15 wherein the cutting surface comprises a burr.

18. The surgical device of claim 15 wherein the electrosurgery comprises coagulation.

19. The surgical device of claim 15 wherein the second member comprises a cutting surface configured to cut tissue mechanically in cooperation with the electrically conductive cutting surface of the first member.

20. The surgical device of claim 19 wherein a portion of the cutting surface of the second member is electrically conductive and is configured to perform electrosurgery along with the cutting surface of the first member.

21. The surgical device of claim 19 wherein the cutting surfaces of the first member and the second member are configured to be moved past each other and to cut tissue mechanically that is disposed between the two cutting surfaces as the two cutting surfaces are moved past each other.

22. The surgical device of claim 15 wherein the second member comprises an electrically insulating cutting surface configured to cut tissue mechanically in cooperation with the electrically conductive cutting surface of the first member.

23. The surgical device of claim 1 wherein the first member is configured to be rotated relative to the second member to cut tissue.

24. The surgical device of claim 23 wherein:
the first member comprises a first tube, and
the second member comprises a second tube, the second tube being cylindrical.

25. The surgical device of claim 1 wherein the first member is substantially electrically insulating, and the first member comprises an electrically conductive material at the distal region of the first member.

26. The surgical device of claim 25 wherein the second member is substantially electrically insulating, and includes an electrically conductive material at the distal region of the second member.

27. The surgical device of claim 1 further comprising:
a drive unit coupled to the first member to move the first member relative to the second member, wherein the second member is fixed with respect to the drive unit;
a first electrode in electrical contact with the distal region of the first member, the first electrode including a cutting surface configured to cut tissue mechanically and to perform electrosurgery; and
a second electrode physically coupled to the second member and electrically isolated from the distal region of the first member,
wherein the distal region of the first member comprises a tip of the first member and the distal region of the second member comprises a tip of the second member.

28. A method of performing surgery, the method comprising:
inserting a surgical device into a body, the surgical device including a first member and a second member, the second member defining a lumen for receiving the first member,
moving the first member and second member relative to each other to cut tissue;
holding a distal region of the first member in electrical contact with a distal region of the second member; and
providing electrical power to the first member through the second member,
wherein:
inserting the surgical device comprises inserting a surgical device having an inner cutting surface on the first member and an outer cutting surface on the second member;
moving the first member and the second member relative to each other comprises cutting tissue in the body using the inner cutting surface and the outer cutting surface; and
providing electrical power further includes performing electrosurgery on the cut tissue using the inner cutting surface.

29. The method of claim 28 further comprising maintaining a distal tip of the first member in electrical connection with a distal tip of the second member.

30. The method of claim 28 wherein moving the first member and second member relative to each other comprises rotating the first member relative to the second member, such rotating causing the inner cutting surface to pass by the outer cutting surface and causing tissue disposed between the two cutting surfaces to be cut mechanically.

31. The method of claim 28 further comprising providing a conductive environment in the body, and wherein inserting the surgical device into the body includes inserting the inner cutting surface into the conductive environment.

32. The method of claim 28 wherein performing electrosurgery comprises performing bipolar electrosurgery using the inner cutting surface as an electrode.

33. The method of claim 32 wherein inserting the surgical device comprises inserting a surgical device that includes a third member coupled to the second member and including a return electrode.

34. A surgical device comprising:
a first member that defines an inner lumen operable as an aspiration lumen;
a second member defining a lumen for receiving the first member, the first member and the second member being configured to be movable with respect to each other to cut tissue;
an electrical connector physically and electrically coupled to the second member for electrically coupling the second member to a source of electricity; and
means for holding a distal region of the first member in electrical contact with a distal region of the second member.

35. A surgical device comprising:
a first member;
a second member defining a lumen for receiving the first member, the first member and second member being configured to be movable with respect to each other to cut tissue;
an electrical connector physically and electrically coupled to the second member for electrically coupling the second member to a source of electricity, wherein the second member comprises a tube and the electrical connector comprises a three-point connector that is self-centering on the tube; and
a tension device for holding a distal region of the first member in electrical contact with a distal region of the second member.

36. A surgical device comprising:
a first member;
a second member defining a lumen for receiving the first member, the first member and second member being configured to be movable with respect to each other to cut tissue;
an electrical connector physically and electrically coupled to the second member for electrically coupling the second member to a source of electricity;
a tension device for holding a distal region of the first member in electrical contact with a distal region of the second member; and
a third member physically coupled to the second member and electrically isolated from the distal region of the first member,
wherein:
the surgical device further comprises a first electrode in electrical contact with the distal region of the first member,
the third member comprises a second electrode, and
the surgical device is operable as a bipolar electrosurgical device using the first electrode and the second electrode.

37. The surgical device of claim 36 wherein:
the first member comprises a first tube,
the second member comprises a second tube, the second tube being cylindrical, and
the third member comprises a third tube disposed about the second tube.

38. The surgical device of claim 36 wherein an exposed surface area of the second electrode is at least approximately five times larger than an exposed surface area of the first electrode.

39. A surgical device comprising:
a first member;
a second member defining a lumen for receiving the first member, the first member and second member being configured to be movable with respect to each other to cut tissue;
an electrical connector physically and electrically coupled to the second member for electrically coupling the second member to a source of electricity; and
a tension device for holding a distal region of the first member in electrical contact with a distal region of the second member,
wherein the first member comprises an electrically conductive cutting surface configured to cut tissue mechanically and to perform electrosurgery and the cutting surface comprises a burr.

40. A surgical device comprising:
a first member;
a second member defining a lumen for receiving the first member, the first member and second member being configured to be movable with respect to each other to cut tissue;
an electrical connector physically and electrically coupled to the second member for electrically coupling the second member to a source of electricity; and
a tension device for holding a distal region of the first member in electrical contact with a distal region of the second member,
wherein the first member comprises an electrically conductive cutting surface configured to cut tissue mechanically and to perform electrosurgery, and the second member comprises a cutting surface configured to cut tissue mechanically in cooperation with the electrically conductive cutting surface of the first member.

41. The surgical device of claim 40 wherein a portion of the cutting surface of the second member is electrically conductive and is configured to perform electrosurgery along with the cutting surface of the first member.

42. The surgical device of claim 40 wherein the cutting surfaces of the first member and the second member are configured to be moved past each other and to cut tissue mechanically that is disposed between the two cutting surfaces as the two cutting surfaces are moved past each other.

43. A surgical device comprising:
a first member;
a second member defining a lumen for receiving the first member, the first member and second member being configured to be movable with respect to each other to cut tissue;
an electrical connector physically and electrically coupled to the second member for electrically coupling the second member to a source of electricity; and
a tension device for holding a distal region of the first member in electrical contact with a distal region of the second member,
wherein the first member comprises an electrically conductive cutting surface configured to cut tissue mechanically and to perform electrosurgery, and the second member comprises an electrically insulating cutting surface configured to cut tissue mechanically in cooperation with the electrically conductive cutting surface of the first member.

44. A surgical device comprising:

a first member;

a second member defining a lumen for receiving the first member, the first member and second member being configured to be movable with respect to each other to cut tissue;

an electrical connector physically and electrically coupled to the second member for electrically coupling the second member to a source of electricity; and a tension device for holding a distal region of the first member in electrical contact with a distal region of the second member, wherein:
the first member is configured to be rotated relative to the second member to cut tissue,
the first member comprises a first tube, and
the second member comprises a second tube, the second tube being cylindrical.

45. A surgical device comprising:

a first member;

a second member defining a lumen for receiving the first member, the first member and second member being configured to be movable with respect to each other to cut tissue;

an electrical connector physically and electrically coupled to the second member for electrically coupling the second member to a source of electricity; and a tension device for holding a distal region of the first member in electrical contact with a distal region of the second member, wherein the first member is substantially electrically insulating, and the first member comprises an electrically conductive material at the distal region of the first member.

46. The surgical device of claim 45 wherein the second member is substantially electrically insulating, and includes an electrically conductive material at the distal region of the second member.

47. A surgical device comprising:

a first member;

a second member defining a lumen for receiving the first member, the first member and second member being configured to be movable with respect to each other to cut tissue;

an electrical connector physically and electrically coupled to the second member for electrically coupling the second member to a source of electricity;

a tension device for holding a distal region of the first member in electrical contact with a distal region of the second member;

a drive unit coupled to the first member to move the first member relative to the second member, wherein the second member is fixed with respect to the drive unit;

a first electrode in electrical contact with the distal region of the first member, the first electrode including a cutting surface configured to cut tissue mechanically and to perform electrosurgery; and a second electrode physically coupled to the second member and electrically isolated from the distal region of the first member, wherein the distal region of the first member comprises a tip of the first member and the distal region of the second member comprises a tip of the second member.

* * * * *